(12) United States Patent
Meyer et al.

(10) Patent No.: US 7,713,624 B2
(45) Date of Patent: May 11, 2010

(54) LUMINESCENT CORE/SHELL NANOPARTICLES SUITABLE FOR (F)RET-ASSAYS

(75) Inventors: Christiane Meyer, Hamburg (DE); Markus Haase, Osnabrück (DE); Werner Hoheisel, Köln (DE); Kerstin Bohmann, Köln (DE)

(73) Assignees: Bayer Technology Services GmbH, Leverkusen (DE); Centrum fur Angewandte Nanotechnologie (CAN) GmbH, Hamburg (DE)

( * ) Notice: Subject to any disclaimer, the term of this patent is extended or adjusted under 35 U.S.C. 154(b) by 652 days.

(21) Appl. No.: 10/554,765

(22) PCT Filed: Apr. 29, 2004

(86) PCT No.: PCT/EP2004/004574

§ 371 (c)(1), (2), (4) Date: Nov. 2, 2006

(87) PCT Pub. No.: WO2004/096944

PCT Pub. Date: Nov. 11, 2004

(65) Prior Publication Data

US 2007/0087195 A1    Apr. 19, 2007

(30) Foreign Application Priority Data

Apr. 30, 2003 (EP) .................. 03009704

(51) Int. Cl.
   *B32B 5/16* (2006.01)
   *C09K 11/08* (2006.01)
(52) U.S. Cl. .............. 428/403; 252/301.4 R; 252/301.4 P; 252/301.4 S; 252/301.4 H; 427/212; 977/773; 977/834; 977/890; 977/896; 977/900

(58) Field of Classification Search ................ 428/403; 525/301.4 R, 301.4 P, 301.4 S, 301.4 H; 977/773, 977/834, 890, 896, 900; 427/212
See application file for complete search history.

(56) References Cited

U.S. PATENT DOCUMENTS

| | | | |
|---|---|---|---|
| 5,674,698 A | 10/1997 | Zarling et al. | |
| 6,207,229 B1 | 3/2001 | Bawendi et al. | |
| 6,815,064 B2 * | 11/2004 | Treadway et al. | 428/403 |
| 6,833,086 B2 * | 12/2004 | Kajiwara | 252/301.6 S |

(Continued)

FOREIGN PATENT DOCUMENTS

| | | |
|---|---|---|
| DE | 101 31 173 | 1/2003 |
| JP | 01-318078 | * 12/1989 |
| WO | WO 00/38282 | 6/2000 |
| WO | WO 01/86299 A2 | 11/2001 |
| WO | WO 02/20696 A1 | 3/2002 |

OTHER PUBLICATIONS

Lemyre & Ritcey, Synthesis of luminescent inorganic nanoparticles for dispersion in organic media, TNT2004 Poster, Sep. 13-17, 2004.*

(Continued)

*Primary Examiner*—H. (Holly) T. Le
(74) *Attorney, Agent, or Firm*—Scully, Scott, Murphy & Presser, P.C.

(57) ABSTRACT

Luminescent inorganic nanoparticles comprising: (a) a core made from a first metal salt or oxide being surrounded by (b) a shell made from a second metal salt or oxide being luminescent and having non-semiconductor properties. These nanoparticles can be advantageously used in (fluorescence) resonance energy transfer ((F)RET)-based bioassays in view of their higher (F)RET efficiency.

29 Claims, 7 Drawing Sheets

U.S. PATENT DOCUMENTS

| | | |
|---|---|---|
| 2001/0024088 A1 | 9/2001 | Justel et al. |
| 2003/0017264 A1 | 1/2003 | Treadway et al. |
| 2003/0032192 A1 | 2/2003 | Haubold et al. |
| 2005/0064604 A1 | 3/2005 | Bohmann et al. |

OTHER PUBLICATIONS

Riwotzki et al, "Liquid-Phase Synthesis of Doped Nanoparticles: Colloids of Luminescing LaPO:Eu and CePO:Tb Particles with a Narrow Particle Size Distribution", J. PHys. Chem. B 2000, 104, 2824-2828.*

M. Hasse et al., *Journal of Alloys and Compounds*, vol. 303-304 (2000) pp. 191-197 "Synthesis and Properties of Colloidal Lanthanide-doped Nanocrystals".

S.C. Farmer et al., *Chemistry of Materials*, American Chemical Society, vol. 13, No. 11 (2001) pp. 3920-3926 "Photoluminescent Polymer/Quantum Dot Composite Nanoparticles".

Official Action dated Nov. 21, 2009 received from the Japanese Patent Office.

* cited by examiner

LUMINESCENT CORE/SHELL NANOPARTICLES SUITABLE FOR (F)RET-ASSAYS

The present application relates to luminescent, in particular photoluminescent nanoparticles having a core of a metal salt or oxide, surrounded by a luminescent shell, the synthesis of these particles and their use in (F)RET-assays, in particular bioassays.

BACKGROUND OF THE PRESENT INVENTION

Over the last decade, nanoparticles, i.e. particles having sizes below 1 micrometer, have attracted a great deal of interest in research and industry due to their unique properties. Research and development in the optoelectronic area have focused on luminescent particles in view of their possible application in light emitting diodes (LED), displays, optoelectronic devices in nanometer dimensions or as a light source in low threshold lasers.

Among luminescent materials, a distinction is often made between semiconductor and non-semiconductor materials.

Semiconductor nanoparticles (often referred to as "quantum dots", such as II-VI or III-V semiconductors which may be doped or not, are characterized by a quantum confinement of both the electron and hole in all three dimensions which leads to an increase in the effective band gap of the material with decreasing crystalline size. Consequently, it is possible to shift both the optical absorption and emission of semiconductor nanoparticles to the blue (higher energies) as the size of the nanoparticles gets smaller.

Water-soluble core/shell semiconductor nanocrystals are, for instance, described in WO 00/17655.

If being compared with quantum dots, it constitutes the particular attractivity of nanocrystalline non-semiconductor-based luminescent materials, in particular, lanthanide-doped metal oxides or salts, that their fluorescent emission is relatively narrow and does not depend to a greater extent on the host material and the size of the nanoparticles. It is rather only the type of lanthanide metal which determines the emission color. PCT/DE 01/03433 assigned to the same applicants discloses a generally applicable synthesis method for lanthanide-doped nanoparticles of this type. These nanoparticles can be produced in sizes (below 30 nm) no longer interacting with the wavelength of visible light, thereby leading to transparent dispersions, e.g., in organic or aqueous solvents.

Other publications relating to lanthanide-doped non-semiconductor based luminescent nanoparticles are, for instance:

K. Riwotzki et al.: *Angewandte Chemie, Int. Ed.* 40, 2001, pages 573-576 with respect to $LaPO_4$:Ce,Tb;

K. Riwotzki, M. Haase, *J. Phys. Chem. B*; Vol. 102, 1998, pages 10129-10135 with respect to $YVO_4$:Eu, $YVO_4$:Sm and $YVO_4$:Dy;

H. Meyssamy, et al., *Advanced Materials*, Vol. 11, Issue 10, 1999, pages 840-844 with respect to $LaPO_4$:Eu, $LaPO_4$:Ce and $LaPO_4$:Ce,Tb;

K. Riwotzki et al., *J. Phys. Chem. B* 2000, Vol. 104, pages 2824-2828, <<(Liquid phase synthesis doped nanoparticles: colloids of luminescent $LaPO_4$:Eu and $CePO_4$:Tb particles with a narrow particle size distribution>>;

M. Haase et al., *Journal of Alloys and Compounds,* 303-304 (2000) 191-197, "Synthesis and properties of colloidal lanthanide-doped nanocrystals";

Jan W. Stouwdam and Frank C. J. M. van Veggel, *Nano Letters*, ASAP article, web release May 15, 2002, "Near-infrared emission of redispersible $Er^{3+}$, $Nd^{3+}$ and $Ho^{3+}$ doped $LaF_3$ nanoparticles"; and G. A. Hebbink et al., *Advanced Materials* 2002, 14, No. 16, pages 1147-1150, "Lanthanide(III)-doped nanoparticles that emit in the near-infrared"

Semiconductor-based nanoparticles ("quantum dots") have already been considered for use in bioassays. Bawendi et al., *Physical Review Letters*, 76, 1996, pages 1517-1520, report, for instance, FRET-effects in specifically labeled biological systems. Further, WO 00/29617 discloses that proteins or nucleic acids can be detected by means of "quantum dots" as label in (F)RET assays. U.S. Pat. No. 6,468,808 B1 and U.S. Pat. No. 6,326,144 B1 also describe biomolecular conjugates of quantum dots and their use in fluorescence spectroscopy.

(F)RET (fluorescence resonance energy transfer) and the related resonance energy transfer (RET) are based on the transfer of excitation energy from a donor capable of emitting fluorescence to an acceptor in close vicinity. With this technique it is possible, for instance with suitable fluorescent labels in biological systems, to determine distances on a molecular level in the range of from about 1 to 8 nm. The energy transferred to the acceptor can relax without emission by internal conversion (RET) and then leads only to the cancellation (quenching) of the donor fluorescence. Alternatively, the acceptor emits the accepted energy also in the form of fluorescence (FRET). These phenomena are well understood and, in the case of dipole-dipole interaction between donor and acceptor, can be explained by the theory of Förster (for instance, J. R. Lakowicz, *Principles of Fluorescence Spectroscopy*, Kluwer Academic Press, New York, 1990, pages 368-445). The energy transfer reduces the intensity of the donor fluorescence as well as its lifetime and simultaneously initiates, sensitizes, or increases the acceptor fluorescence. The efficiency of the energy transfer is dependent on the inverse 6th power of the intermolecular separation and decreases proportionally to $R_0^6/(R_0^6+R^6)$. $R_0$, the so-called Förster radius characterizes that distance between donor and acceptor for which the efficiency of the energy transfer is 50%.

The F(RET) efficiency can be either determined via the fluorescence intensity of the donor with acceptor $(Q_{DA})$ and without acceptor $(Q_D)$, respectively, by means of the equation $1-(Q_{DA}/Q_D)$ or by comparing the lifetimes of the donor in the presence $(T_{DA})$ of and absence $(T_D)$ of the acceptor probe on the basis of the equation $1-(T_{DA}/T_D)$.

The use of "quantum dots" in bioassays suffers, however, from various disadvantages. Since the emission wavelengths of fluorescent "quantum dots" depends on the size of the particles, only a very narrow size distribution can be used. This represents a challenge for synthesis and/or size selection techniques. Moreover, "quantum dots" normally show relatively low quantum efficiencies which is caused by emission-free electron-hole pair recombinations. To overcome this deficiency, CdSe/CdS core/shell structures have been proposed wherein the CdS coating protects and enhances the photostability of the luminescent CdSe core (X. Peng et al., *J. Am. Chem. Soc.* 119, 1997, pages 7019-7029).

Typically, (F)RET-based assays are conducted with organic dye molecules, such as fluoresceine or rhodamine. For many applications a general drawback associated with these organic fluorescent dyes is their insufficient stability towards incident light. Their photo-toxicity can further damage biological material in the close environment. Other undesirable properties are their broad emission bands and the small stoke shifts, i.e. the difference between excitation and emission maximum, as well as the relatively narrow spectral excitation bands which require often the use of several light sources and/or complicated photo systems.

Accordingly, it is one object of the present invention to provide fluorescent inorganic materials which are particularly suitable for (F)RET-assays, in particular bioassays, and overcome the above-mentioned disadvantages.

It is a further object of the present invention to increase the (F)RET efficiency. A higher (F)RET efficiency increases the sensitivity of the method and improves for instance the signal/noise ratio.

In addition, (F)RET-based assays require donor molecules having high quantum yields (the ratio of emitted to absorbed protons) in order to increase the overall sensitivity of the assay. Therefore, it is a further object of the present invention to provide inorganic fluorescent particles having high quantum yields, which make them also particularly attractive for other applications than in bioassays.

According to a further object of the present invention, a specific process for the manufacture of these fluorescent materials is to be provided.

Finally, it is an object to provide a bioassay based on inorganic nanoparticulate materials.

SUMMARY OF THE PRESENT INVENTION

The above technical objects have been solved by luminescent inorganic nanoparticles comprising
(a) a core made from a first metal salt or oxide being surrounded by
(b) a shell made from a second metal salt or oxide being luminescent and having non-semiconductor properties.

and the process for their manufacture as laid down below.

DETAILED DESCRIPTION OF THE PRESENT INVENTION

I. Luminescent Nanoparticles

Figure 1:
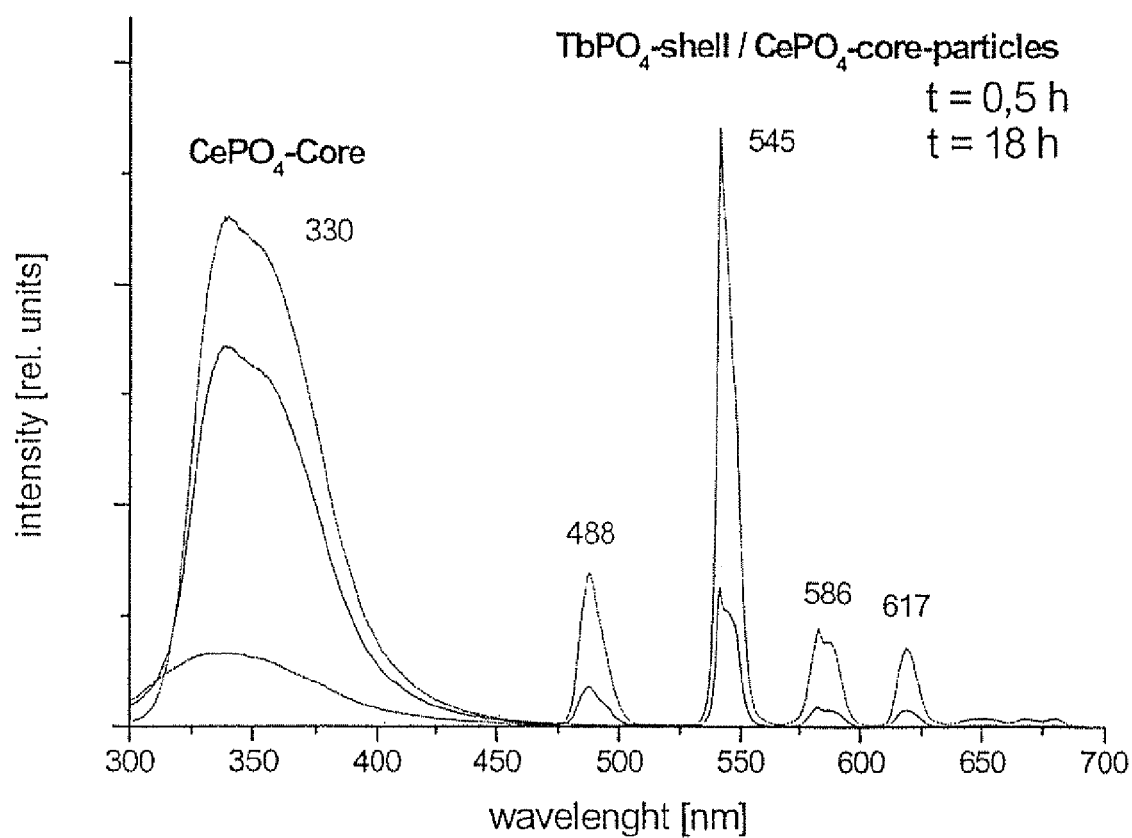
FIG. 1 shows the fluorescence spectra of homogeneous $CePO_4$ core particles and $CePO_4/TbPO_4$ core/shell particles according to the present invention.

The luminescent, in particular photoluminescent particles of the present invention comprise (a) a core made from a first metal salt or oxide being surrounded by (b) a luminescent, non-semiconductor shell made from a second metal salt or oxide.

"Luminescence" characterizes the property of the claimed nanoparticles to absorb energy (e.g., in the form of photons (IR, visible, UV), electron rays, X-ray, etc.) which is then emitted as light of lower energy. It is to be understood that the term "luminescent" throughout the description and the claims also includes the more specific and preferred meaning "photoluminescent"

As "photoluminescence", we understand the capability of the inorganic metal salt to absorb photons of a specific energy (e.g. UV, visible) and emit light of lower energy (longer wavelength, e.g. UV, visible, IR) over a certain period of time. The period of light emission can correspond to life-times of the excited state up to $10^{-7}$ or $10^{-8}$ sec, which are typically referred to as fluorescence, but also much longer. For lanthanide-doped salts, e.g. sulfates, phosphates or fluorides, typically lifetimes of the excited state in the order of milliseconds (for instance 1-20 ms) are observed.

According to the present invention it is preferred that both shell and core material do not show semiconductor properties.

Both shell and core preferably also constitute crystalline materials. This can be confirmed by X-ray powder diffraction patterns.

The shape of the claimed core/shell particles can be for instance needle like, ellipsoid or spherical, the latter two options being preferred.

The claimed core/shell nanoparticles preferably have an average size measured along their longest axis of 1 to 100 nm, more preferably 1 to 50 nm. Average sizes of maximally 30 nm, maximally 20 nm, maximally 10 nm, for instance 2 to 8 nm, or 4-6 nm are even more desirable. In each case, the standard derivation is preferably less than 30%, in particular less than 10%.

The particle size and distribution can be measured according to techniques further described in the already-cited articles by K. Riwotzki et al and M. Haase et al, for instance, with transmission electromicrographs (TEM). Gel permeation chromatography and ultra-centrifugation also allow determining the size.

The thickness of the shell is preferably at least two monolayers. A preferred upper limit for the shell thickness are two diameters of the core (for non-spheroidal particles measured along the longest axis), more preferably one core diameter, e.g. ⅔ thereof.

According to the first embodiment of the present invention, the core (a) is made from a metal salt or oxide, which does not accept energy from the shell after its electronic excitation, in particular a non-luminescent metal salt or oxide and (b) the shell is made from a luminescent, in particular doped metal salt or oxide.

Throughout the present application "doping" is to be understood in a broad sense. The upper limit of dopant to be used should be low enough that the generated luminescence is not reduced by concentration quenching phenomena. Correspondingly, this upper limit depends on factors like the type of doping ion and the distance between the dopant metal ions in the lattice which are specific to each core material. Preferably, the host material is substituted by the dopant in an amount of up to 50 mol %, preferably 0.1 to 45 mol %, e.g. 0.5 to 40 mol %, or 1 to 20 mol %.

There are also no specific restrictions regarding the type of dopant metal to be incorporated, as long as the same is capable of converting absorbed photons to luminescent radiation. Thus, for instance metals like Ag, Cu, Co or Mn (for instance, in combination with zinc as host metal) can be used. Doping with lanthanide metals is however preferred since the luminescence of lanthanide metals is particularly independent from its lattice environment. Generally, the use of bi- or trivalent dopants, in particular lanthanide dopants is preferred. Bivalent lanthanides (+II oxidation state) are characterized by a relatively strong absorption, but relatively broad emission bands. For this reason, they can be suitably used as sensitizer transferring the energy to other luminescing metals (e.g. $Eu^{2+}$ to $Mn^{2+}$). The capacity of trivalent lanthanides (oxidation state +III) to emit light in the form of relatively sharp bands makes them particularly attractive dopants for single use although, as explained later, also suitable combinations of trivalent lanthanides dopant systems exist.

Suitable dopant materials for the shell include Al, Cr, Tl, Mn, Ag, Cu, As, Nb, Ni, Ti, In, Sb, Ga, Si, Pb, Bi, Zn, Co which, depending on the host material used, have luminescent properties, in particular Mn, Ag, Cu, Bi, Cr, Sn, Sb and preferably the lanthanides, in particular Ce (58), Pr (59), Nd (60), Sm (62), Eu (63), Gd (64), Tb (65), Dy (66), Ho (67), Er (68), Tm (69), or Yb (70) or combinations thereof.

Doping with lanthanide metals is preferred since the luminescence of lanthanide metals is particularly independent from its lattice environment.

From a practical point of view (type of fluorescence, intensity, etc.) Ce, Tb, Eu, Nd, Dy, Th, Sm, Gd, Ho, Er and Yb show the most interesting luminescence properties.

$Er^{3+}$, $Nd^{3+}$ and $Ho^{3+}$ are of particular interest for the telecommunication area since they emit between 1300 and 1600 nm. Ce is preferably used in combination with another dopant material, such as Nd, Dy or Tb. Ce is known to absorb strongly UV radiation having a wavelength of from 250 to 300 nm, but shows a fairly broad luminescence band around 330 nm depending on the host lattice (e.g. phosphate). If used in combination with other dopants to which the absorbed energy can be transferred, very efficient luminescent systems can be generated. Another attractive combination of dopant metals is Yb and Er, which is of great importance in $Er^{3+}$-doped optical amplifiers where $Er^{3+}$ is pumped indirectly via $Yb^{3+}$ which has a ten times higher absorption cross section and a much broader peak at 980 nm than $Er^{3+}$. $Nd^{3+}$ and $Gd^{3+}$ can also be combined.

As indicated before, it is not only possible to use these lanthanide metal combinations as dopants for the shell. It is equally effective to employ as host metal that lanthanide metal ion (e.g. $Ce^{3+}$, $Yb^{3+}$, $Nd^{3+}$) having the higher absorption cross section and replacing a part thereof by lower amounts of the other metal (e.g. $Tb^{3+}$, $Er^{3+}$, $Gd^{3+}$). For this reason, lanthanide salts (e.g. $Ce^{3+}$, $Yb^{3+}$, $Nd^{3+}$ salts) can also be used as the host material of the shell.

For applications in aqueous media as used for biological assays, the most preferred dopants are those (e.g. Tb, Dy, Tm, Sm) showing luminescence in the visible area in order to minimize interaction with water which otherwise may absorb the emitted light.

The host material for the shell is not specifically limited and can be selected from known non-luminescent metal oxides or salts, such as sulfides, selenides, sulfoselenides, oxysulfides, phosphates, halophosphates, arsenates, sulfates, borates, aluminates, gallates, silicates, germanates, oxides, vanadates, niobates, tantalates, tungstates, molybdates, alkalihalogenates, other halides, in particular fluorides, phosphides, or nitrides. The use of sulfates, phosphates or fluorides is particularly preferred.

The metals of these salts preferably belong to the main groups 1, 2, 13, or 14, the subgroups 3, 4, 5, 6, 7, or the lanthanides. Since most luminescent dopants are bi- or trivalent metal ions, it is preferred to use, as counter ion for the shell, non-luminescent bi- or tri-valent metal atoms such as the metals of group 2 (earth alkaline metals, such as Mg, Ca, Sr, or Ba), or group 3 (Sc, V or La) or group 13 (e.g., Al, Ga or In) or Zn.

Preferred embodiments of host metal salts comprise:
phosphates of the corresponding number of metals (to ensure charge neutrality) selected from main group 2 (e.g. from Mg, Ca, Sr, Ba), group 3 (e.g. Sc, Y, La), or lanthanides (elements 58 to 71, i.e. Ce, Pr, Nd, Pm, Sm, Eu, Gd, Tb, Dy, Ho, Er, Tm, Yb and Lu);

sulfates of the corresponding number of metals selected from group 2 (e.g. from Mg, Ca, Sr, Ba), group 3 (e.g. Sc, Y, La), or lanthanides (as above)

borates of the corresponding number of metals selected from main group 2 (e.g. from Mg, Ca, Sr, Ba), group 3 (e.g. Sc, Y, La), or group 13 (Al, Ga, In, Tl) or lanthanides (as above);

fluorides of the corresponding number of metals selected from group 2 (e.g. from Mg, Ca, Sr, Ba), subgroup 3 (e.g. Sc, Y, La), or lanthanides (as above);

aluminates (e.g. $Al_5O_{12}$ or $AlO_4$) of the corresponding number of metal atoms selected from group 2 (e.g. from Mg, Ca, Sr, Ba), group 3 (e.g. Sc, Y, La), or lanthanides (as above);

gallates (e.g. $Ga_5O_{12}$) of the corresponding number of metal atoms selected from group 2 (e.g. from Mg, Ca, Sr, Ba), group 3 (e.g. Sc, Y, La), or lanthanides (as above);

silicates (e.g. $SiO_3$ or $SiO_4$) of the corresponding number of metals selected from group 2 (e.g. from Mg, Ca, Sr, Ba), group 3 (e.g. Sc, Y, La), group 12 (e.g. Zn, Cd) or lanthanides (as above);

vanadates (e.g. $VO_4$) of the corresponding number of metal atoms selected from group 2 (e.g. from Mg, Ca, Sr, Ba), group 3 (e.g. Sc, Y, La), or lanthanides (as above);

tungstates (e.g. $WO_4$) of the corresponding number of metal atoms selected from group 2 (e.g. from Mg, Ca, Sr, Ba), group 3 (e.g. Sc, Y, La), or lanthanides (as above);

molybdates (e.g. $MoO_4$) of the corresponding number of metal atoms selected from group 2 (e.g. from Mg, Ca, Sr, Ba), group 3 (e.g. Sc, Y, La), or lanthanides (as above);

tantalates (e.g. $TaO_4$) of the corresponding number of metal atoms selected from group 2 (e.g. from Mg, Ca, Sr, Ba), group 3 (e.g. Sc, Y, La), or lanthanides (as above); or arsenates (e.g. $AsO_4$) of the corresponding number of metal atoms selected from group 2 (e.g. from Mg, Ca, Sr, Ba), group 3 (e.g. Sc, Y, La), or lanthanides (as above).

When selecting a suitable host material for a specific dopant, it is further to be taken into account, as known in the art, that host and dopant metal preferably should have the same valence and similar (tolerance e.g. ±20%) or identical ion diameters. Simultaneously, it typically increases the compatibility of dopant and host metal if these are capable of forming, with a specific anion, crystals of the same or similar lattice type having the same or similar lattice constant(s) (tolerance e.g. ±20%).

The above criterion can often be met with Ba and La as host material metal for the core since these metals display ion diameters, which are very similar to those of the two-valent (+II) lanthanides. For the same reason, La and Y salts represent suitable host materials for tri-valent (+III) lanthanide dopants.

Specific examples of luminescent shell materials are for instance LiI:Eu; NaI:Tl; CsI:Tl; CsI:Na; LiF:Mg; LiF:Mg,Ti; LiF:Mg,Na; $KMgF_3$:Mn; $Al_2O_3$:Eu; BaFCl:Eu; BaFCl:Sm; BaFBr:Eu; $BaFCl_{0.5}Br_{0.5}$:Sm; $BaY_2F_8$:A (A=Pr, Tm, Er, Ce); $BaSi_2O_5$:Pb; $BaMg_2Al_{16}O_{27}$:Eu; $BaMgAl_4O_{23}$:Eu; $BaMgAl_{10}O_{17}$:Eu; $BaMgAl_2O_3$:Eu; $Ba_2P_2O_7$:Ti; $(Ba,Zn,Mg)_3Si_2O_7$:Pb; $Ce(Mg,Ba)Al_{11}O_{19}$; $Ce_{0.65}Tb_{0.35}MgAl_{11}O_{19}$:Ce, Tb; $MgAl_{11}O_{19}$:Ce,Tb; $MgF_2$:Mn; MgS:Eu; MgS:Ce; MgS:Sm; MgS:(Sm,Ce); (Mg,Ca)S:Eu; $MgSiO_3$:Mn; $3.5MgO.0.5MgF_2.GeO_2$:Mn; $MgWO_4$:Sm; $MgWO_4$:Pb; $6MgO.As_2O_5$:Mn; $(Zn,Mg)F_2$:Mn; $(Zn_4Be)SO_4$:Mn; $Zn_2SiO_4$:Mn; $Zn_2SiO_4$:Mn,As; $Zn_3(PO_4)_2$:Mn; $CdBO_4$:Mn; $CaF_2$:Mn; $CaF_2$:Dy; CaS:A A=Lanthanide, Bi); (Ca,Sr)S:Bi; $CaWO_4$:Pb; $CaWO_4$:Sm; $CaSO_4$:A (A=Mn, lanthanide); $3Ca_3(PO_4)_2.Ca(F,Cl)_2$:$Sb,M_n$; $CaSiO_3$:Mn,Pb; $Ca_2Al_2Si_2O_7$:Ce; $(Ca,Mg)SiO_3$:Ce; $(Ca,Mg)SiO_3$:Ti; $2SrO.6(B_2O_3).SrF_2$:Eu; $3Sr_3(PO_4)_2.CaCl_2$:Eu; $A_3(PO_4)_2.ACl_2$:Eu (A=Sr, Ca, Ba); $(Sr,Mg)_2P_2O_7$:Eu; $(Sr,Mg)_3(PO_4)_2$:Sn; SrS:Ce; SrS:Sm, Ce; SrS:Sm; SrS:Eu; SrS:Eu,Sm; SrS:Cu,Ag; $Sr_2P_2O_7$:Sn; $Sr_2P_2O_7$:Eu; $Sr_4Al_{14}O_{25}$:Eu; $SrGa_2S_4$:A (A=lanthanide, Pb); $SrGa_2S_4$:Pb; $Sr_3Gd_2Si_6O_{18}$:Pb,Mn; $YF_3$:Yb,Er; $YF_3$:Ln (Ln=lanthanide); $YLiF_4$:Ln (Ln=lanthanide); $Y_3Al_5O_{12}$:Ln (Ln=lanthanide); $YAl_3(BO_4)_3$:Nd,Yb; $(Y,Ga)BO_3$:EU; $(Y,Gd)BO_3$:EU; $Y_2Al_3Ga_2O_{12}$:Tb; $Y_2S_2O_5$:Ln (Ln=lanthanide); $Y_2O_3$:Ln (Ln=lanthanide); $Y_2O_2S$:Ln (Ln=lanthanide); $YVO_4$:A (A=lanthanide, In); $Y(P,V)O_4$:Eu; $YTaO_4$:Nb; $YAlO_3$:A (A=Pr, Tm, Er, Ce); YOCl:Yb,Er; $LnPO_4$:Ce,Tb (Ln=lanthanide or mixture of lanthanides); $LuVO_4$:Eu; $GdVO_4$:Eu; $Gd_2O_2S$:Tb; $GdMgB_5O_3O_{10}$:Ce,Tb; LaOBr:Tb; $La_2O_2S$:Tb; $LaF_3$: Nd, Ce; $BaYb_2F_8$:Eu; $NaYF_4$:Yb,Er; $NaGdF_4$:Yb,Er; $NaLaF_4$:Yb,Er; $LaF_3$:Yb, Er, Tm; $BaYF_5$:Yb,Er; $Ga_2O_3$:Dy; GaN:A (A=Pr, Eu, Er, Tm); $Bi_4Ge_3O_{12}$; $LiNbO_3$:Nd,Yb; $LiNbO_3$:Er; $LiCaAlF_6$:Ce; $LiSrAlF_6$:Ce; $LiLuF_4$:A (A=Pr, Tm, Er, Ce); $Li_2B_4O_7$:Mn, $SiO_x$:Er,Al ($0 \leq x \leq 2$); $Y_2O_3$:Ln (Ln=lanthanides, in particular Eu), $Y_2O_2S$:Eu, $Y_2SiO_5$:Eu, $SiO_2$:Dy, $SiO_2$:Al, $Y_2O_3$:Tb, $CaSiO_3$:Ln, CaS:Ln, CaO:Ln, wherein Ln=one, two or more lanthanides.

If classified according to the host lattice type the following preferred embodiments can also be enumerated.

1. Halides: for instance $XY_2$ (X=Mg, Ca, Sr, Ba; Y=F, Cl, I), $CaF_2$:Eu (II), $BaF_2$:Eu; $BaMgF_4$:Eu; $LiBaF_3$:Eu; $SrF_2$:Eu; $SrBaF_2$Eu; $CaBr_2$:Eu—$SiO_2$; $CaCl_2$:Eu; $CaCl_2$:Eu—$SiO_2$; $CaCl_2$:Eu, Mn—$SiO_2$; $CaI_2$:Eu; $CaI_2$EU,Mn; $KMgF_3$:Eu; $SrF_2$:Eu (II), $BaF_2$:EU (II), $YF_3$, $NaYF_4$, :$MgF_2$:Mn; $MgF_2$:Ln (Ln=lanthanide(s)).

2. Earth alkaline sulfates: for instance $XSO_4$ (X=Mg, Ca, Sr, Ba), $SrSO_4$:Eu, $SrSO_4$:Eu,Mn, $BaSO_4$:Eu, $BaSO_4$:EU, Mn, $CaSO_4$, $CaSO_4$:Eu, $CaSO_4$:Eu,Mn, as well as mixed earth alkaline sulfates, also in combination with magnesium, e.g. $Ca,MgSO_4$:Eu,Mn.

3. Phosphates and halophosphates: for instance $CaPO_4$:Ce, Mn, $Ca_5(PO_4)_3Cl$:Ce,Mn, $Ca_5(PO_4)_3F$:Ce,Mn, $SrPO_4$:Ce, Mn, $Sr_5(PO_4)_3Cl$:Ce,Mn, $Sr_5(PO_4)_3F$:Ce,Mn, the latter also codoped with Eu (II) or codoped with Eu,Mn, $\alpha$-$Ca_3(PO_4)_2$:Eu; $\beta$-$Ca_3(PO_4)_2$:Eu, Mn; $Ca_5(PO_4)_3Cl$:Eu; $Sr_5(PO_4)_3Cl$:Eu; $Ba_{10}(PO_4)_6Cl$:Eu; $Ba_{10}(PO_4)_6Cl$:Eu,Mn, $Ca_2Ba_3(PO_4)_3Cl$:Eu; $Ca_5(PO_4)_3F$:$Eu^{2+}X^{3+}$; $Sr_5(PO_4)_3$:$Eu^{2+}X^3$+(X=Nd, Er, Ho, Tb); $Ba_5(PO_4)_3Cl$:Eu; $\beta$-$Ca_3(PO_4)_2$: Zu; $CaB_2P_2O_9$:Eu; $CaB_2P_2O_9$:Eu; $Ca_2P_2O_7$:Eu; $Ca_2P_2O_7$:Eu, Mn; $Sr_{10}(PO_4)_6Cl_2$:Eu; $(Sr, Ca, Ba, Mg)_{10}(PO_4)_6Cl_2$:Eu; $LaPO_4$:Ce; $CePO_4$; $LaPO_4$:Eu, $LaPO_4$:Ce, $LaPO_4$:Ce,Tb, $CePO_4$:Tb.

4. Borates: for instance $LaBO_3$; $LaBO_3$:Ce; $ScBO_3$:Ce $YAlBO_3$:Ce; $YBO_3$:Ce; $Ca_2BsOgCl$:Eu; $XEuO.yNa_2O.zB_2O_3$.

5. Vanadates: for instance $YVO_4$, $YVO_4$:Eu, $YVO_4$:Dy, $YVO_4$:Sm $YVO_4$:Bi; $YVO_4$:Bi,Eu, $YVO_4$:Bi,Dy, $YVO_4$:Bi, Sm, $YVO_4$:Tm, $YVO_4$:Bi,Tm $GdVO_4$, $GdVO_4$:EU, $GdVO_4$:Dy, $GdVO_4$:Sm $GdVO_4$:Bi; $GdVO_4$:Bi,Eu, $GdVO_4$:Bi,Dy, $GdVO_4$:Bi,Sm; $YVO_4$:Eu, $YVO_4$:Sm, $YVO_4$:Dy.

6. Aluminates: for instance $MgAl_2O_4$:Eu; $CaAl_2O_4$:Eu; $SrAl_2O_4$:Eu; $BaAl_2O_4$:Eu; $LaMgAl_{11}O_{19}$:Eu; $BaMgAl_{10}O_{17}$:Eu; $BaMgAl_{10}O_{17}$:Eu, Mn; $CaAl_{12}O_{19}$:Eu; $SrAl_{12}O_{19}$:Eu; $SrMgAlO_{10}O_{17}$:Eu; $Ba(Al_2O_3)_6$:Eu; $(Ba,Sr)MgAl_{10}O_{17}$:Eu, Mn; $CaAl_2O_4$:Eu, Nd; $SrAl_2O_4$:Eu, Dy; $Sr_4Al_{14}O_{25}$:Eu, Dy.

7. Silicates: for instance $BaSrMgSi_2O_7$:Eu; $Ba_2MgSiO_7$:Eu; $BaMg_2Si_2O_7$:Eu; $CaMgSi_2O_6$:Eu; $SrBaSiO_4$:Eu; $Sr_2Si_3O_8SrCl_2$:Eu; $Ba_5SiO_4Br_6$:Eu; $Ba_5SiO_4Cl_6$:Eu; $Ca_2MgSi_2O_7$:Eu; $CaAl_2Si_2O_8$:Eu; $Ca_{1.5}Sr_{0.5}MgSi_2O_7$:Eu; $(Ca, Sr)_2MgSi_2O_7$:Eu, $Sr_2LiSiO_4F$:Eu.

8. Tungstates and molybdates: for instance $X_3WO_6$ (X=Mg, Ca, Sr, Ba), $X_2WO_4$ (X=Li, Na, K, Rb, Cs), $XMoO_4$ (X=Mg, Ca, Sr, Ba) as well as polymolybdates oder polytungstates or the salts of the corresponding hetero-oder isopolyacids.

9. Germanates: e.g. $Zn_2GeO_4$ 10. moreover the following classes: $ALnO_2$:Yb, Er (A=Li, Na; Ln=Gd, Y, Lu); $Ln_2O_3$:Yb, Er (Ln=La, Gd, Y, Lu); $LnAO_4$:Yb, Er (Ln=La, Y; A=P, V, As, Nb); $Ca_3Al_2Ge_3O_{12}$:Er; $Gd_2O_2S$:Yb, Er; $La_2S$:Yb, Er.

According to the first embodiment of the present invention, the core material, i.e. a metal salt or oxide, does not accept energy transfer from the luminescent shell in its electronically excited state.

This requirement can be always met with core metal salts or oxides having only electronic states wherein the energetic distance between the electronic ground state and the first electronically excited state is greater than the distance between the first electronically excited state of the selected luminescent shell and its ground state. Under these circumstances the energy (e.g. UV, visible, IR) absorbed by the shell cannot be transmitted to the core metal atoms or anions. The localization of the energy in the shell achieved thereby enhances surface quenching phenomena and is believed to increase the overall (F)RET efficiency of the particle. According to one preferred embodiment, the core salt or oxide is non-luminescent and thus lacking absorption bands (UV-vis or IR) to which the energy could be transferred from the excited shell. Since non-luminescent materials are often cheaper than luminescent materials, this is also economically of advantage.

Preferably, the core material corresponds to the host material of the doped shell.

Suitable anions forming the core are thus the same as indicated above and involve, but are not limited to phosphates, halophosphates, arsenates, sulfates, borates, aluminates, gallates, silicates, germanates, oxides, vanadates, niobates, tantalates, tungstates, molybdates, alkalihalogenates, other halides, or nitrides. Nanoparticulate metal salts of this type are disclosed in PCT/DE 01/03433.

The only criteria governing the selection of the core metal atoms is their lacking capability to accept luminescence from the shell after irradiation with photons. Preferred metal ions, which can be used for this purpose, are the same as mentioned above for the host material of the shell. They include, but are not limited to metals of group 2 (earth alkaline metals, such as Mg, Ca, Sr or Ba), metals of group 3 (such Sc, Y or La), zinc, or metals of group 13 (such Al, Ga, or In). In order to increase the aptitude of the shell material to grow on the surface of the core material, it is further preferred, but not absolutely necessary to select as core material the same salt that constitutes the host of the doped shell. If this requirement is not fulfilled, it is preferred that the host material of the core and the shell material belong to the same lattice type and display very similar (tolerance e.g. ±20%) or identical lattice constants.

According to the second embodiment, (a) the core comprises a first metal salt or oxide ("donor") which after excitation is capable of transferring the excitation energy to (b) a second shell-forming luminescent metal salt or oxide ("acceptor") which emits the same as luminescence.

Suitable donor-acceptor metal combinations can for instance be selected among the above-identified dopants, in particular lanthanides and generally require a distance between the electronic ground state and the first excited state of the donor metal which involves a higher energy than the corresponding distance of the acceptor metal.

Examples for suitable photon energy absorbers (donors), which can be used as core material in the second embodiment of the invention, are lanthanide ions having relatively high absorption cross-sections such as $Ce^{3+}$, $Yb^{3+}$, $Nd^{3+}$ or $Eu^{2+}$. $Ce^{3+}$ is preferably used in combination with $Tb^{3+}$, $Dy^{3+}$ or $Nd^{3+}$ as shell material metal and acceptor, e.g. in the form of the corresponding sulfates, phosphates or fluorides.

$Yb^{3+}$ salts, such as phosphates, sulfates or fluorides are preferably combined as core material with $Er^{3+}$ salts, such as sulfates, phosphates or fluorides, respectively, as shell material. This allows pumping $Er^{3+}$ indirectly via $Yb^{3+}$.

In terms of shell constitution, the acceptor atoms can be used as high concentration dopant materials of the host materials described in the context of the first embodiment of the present invention. However, it is also possible that the entire shell consists of the corresponding acceptor salt, e.g. metal sulfate, phosphate or fluoride in order to increase the efficiency of energy transfer from the core to the shell.

The core material of the second embodiment may comprise the donor metal as high concentration dopant of a host material as described above. Alternatively and preferably, the core consists of the corresponding donor metal salt.

The anion of the core salt can be freely selected among compatible anions allowing the growth of the selected shell material. Examples of suitable anions are given for the first embodiment, sulfate, phosphate or fluoride being preferred.

One particular preferred example for the so-called second embodiment are $CePO_4/TbPO_4$ core/shell particles.

In accordance with the second embodiment, it is also possible to employ vanadates, molybdates, tungstates or germanates as core materials (donor) since the corresponding anions are also capable of absorbing energy and transferring the same to a suitable shell material (acceptor) which then emits the energy as luminescence. These may also be combined with dopant metals acting itself as luminescent centers and thus enhancing luminescence, such as $Bi^{3+}$ and/or $Eu^{3+}$ for vanadates. The core may for instance comprise or consists of vanadates, molybdates, tungstates or germanates of metals of group 3 (such Sc, Y or La) or metals of group 13 (such Al, Ga, or In). It is preferably combined with lanthanide salts, preferably phosphates, vanadates, molybdates, tungstates or germinates as shell material wherein the lanthanide acts as energy acceptor. Specific examples involve core/shell combinations of the type $LaVO_4/EuPO_4$, $LaVO_4/NdPO_4$, $YVO_4/DyPO_4$.

II. Synthesis of Core/Shell Nanoparticles

The above-described core/shell nanoparticles of the present invention are synthesised in a process as laid down below and in the claims which comprises at least the following two steps:

1. The preparation of a so-called "first mixture" comprising nanoparticles of a first metal salt or oxide, e.g. metal sulfate, phosphate or fluoride nanoparticles (cores) in an organic medium.
2. Reacting said first mixture, an anion source for the shell to be formed, in particular a phosphate, sulfate or fluoride source, and a "second mixture" comprising shell-forming metal ions and an organic complexing agent for said metal ions at a temperature of 50 to 350° C. until a shell has formed around said nanoparticle cores.

II.1 First Process Step and Synthesis of Core Particles

The nanoparticles provided as core material and being present in the so-called "first mixture" can be synthesized according to processes known in the art.

Generally, wet synthesis techniques are preferred over dry formation processes since the former allow a better control of the particle sizes. Furthermore, the aggregation of the formed nanoparticles can be more easily suppressed in wet synthesis techniques.

Among the known wet synthesis techniques, for instance sol-gel processes, the hydrothermal synthesis, or the organic synthesis with complexing agents that regulate crystal growth can be used. Further, it is possible to produce specifically the fluorides in a synthesis technique described in the already mentioned article by J. W. Stouwdam and F. C. J. M. Van Veggel. Accordingly, $LaF_3$ nanoparticles and other fluorides can be prepared by heating a solution of ammonium di-n-octadecyldithiophosphate and NaF in ethanol/water. Subsequently, solutions of the corresponding metal nitrates in water are added dropwise, followed by stirring the solution two hours at 75° C. and cooling to room temperature. The disadvantage of this technique, however, is that the generated particles still display a relatively broad particle size distribution which necessitates further purification steps by centrifugation.

The "hydrothermal synthesis" of lanthanide-doped phosphates is, for instance, described in "Wet-chemical synthesis of doped colloidal nanomaterials: particles and fibres of $LaPO_4$:Eu, $LaPO_4$:Ce and $LaPO_4$:Ce,Tb" by H. Meyssamy et al, Advanced Materials (1999), Vol. 11, No. 10, pages 840 et seq.

As starting materials for sulfate, phosphate or fluoride nanoparticles, preferably metal chlorides, nitrates or acetates are used. The reaction is performed in water as reaction medium in an autoclave to maintain high pressures, preferably pressures of from 10-20 bar during the reaction.

The hydrothermal synthesis results in relatively large particles which often have a needle-like shape. Further, a relatively broad distribution of particle sizes typically characterizes the product. In the above-named method by H. Meyssamy et al, the percentage of nanoparticles with diameters of less than 25 nm is, for instance, only around 20%. These can be isolated by subsequent centrifugation steps.

Other examples for the hydrothermal synthesis can be found in PCT/DE 01/03433. This document discloses, on a more general level and by means of concrete examples, the synthesis of nanoparticulate silicates, vanadates, tungstates, molybdates, tantalates, etc. in water under high pressures (autoclave). Further, this document pertains to a related technique for the synthesis of aluminates or gallates in 1,6-hexanediol (therein also referred to as "glycothermal" synthesis).

Further, it is possible to produce optionally doped sulfates under ambient pressure in organic media selected from polyols and sulfoxides, which are believed to regulate crystal growth by metal-complexing activity. This technique will be referred to in the following as "polyol or sulfoxide synthesis".

The polyols to be used preferably have two or three hydroxy groups and can be exemplified by glycerol, ethylene glycol or polyethylene glycol, whereby preferably low molecular weight polyethylene glycol is used (preferred average number of ethylene glycol units up to 4). As sulfoxide dimethylsulfoxide (DMSO) may be used. This synthesis technique is preferably employed in the preparation of earth alkaline metal sulfates, such as magnesium, calcium, strontium or barium sulfate as doped host material.

Preferred metal atom sources are the corresponding chlorides and their hydrates. As starting material for the sulfate, preferably alkali metal sulfates, ammonium sulfates or sulfates having an organic cation are employed. The corresponding hydrogensulfates are equally suitable.

The organic cation is preferably selected from basic N-containing aliphatic, aromatic and aliphatic/aromatic substances which preferably have from 4 to 30, preferably from 4 to 20 carbon atoms. Suitable cations involve, for instance, quaternary ammonium or phosphonium wherein the four substituents can be independently selected from alkyl having preferably from 1 to 10 carbon atoms (preferably 1 to 5) or benzyl, or protonated aromatic bases, such as hydrazine, amantadine, pyridine or collidine.

Correspondingly, sulfate nanoparticles can be produced from starting materials such as tetrabutylammonium hydrogensulfate, tetramethylammonium sulfate, bis-tetrabutylammonium sulfate, or triethylammonium hydrogensulfate. Other suitable starting materials are ammonium hydrogensulfate, ammonium sulfate, alkali metal hydrogensulfates, amantadine sulfates, ethylenediammonium sulfate and hydrazinium sulfate.

For doping the sulfate host material, nitrates or halides of the corresponding dopant, in particular the corresponding metal chloride can be used.

If hydrogensulfates are contained in the starting material, organic bases such as imidazol are preferably added as acid scavenger to the reaction medium. The reaction is preferably conducted at temperatures of from 50 to 240° C., whereby the lower temperature range of from 50 to 100° C. is preferred for glycerol and higher temperatures in the range from 160 to 240° C., in particular 160 to 180° C. are most suitable for the other polyol or sulfoxide solvents. The particles obtained have an average diameter in the order of 0.2 to 50 nm and are readily dispersible in aqueous media.

Nanoparticle cores obtained by sol-gel processes, the hydrothermal synthesis, glycothermal synthesis or the so-called "polyol or sulfoxide synthesis" are sometimes not dispersible in the organic medium to be used in the first step of the claimed method, especially if the reaction medium for the core and the method of the invention (shell synthesis), respectively, differ considerably in terms of polarity. For this reason, it may become necessary to subject the nanoparticles to an after-treatment with a suitable polar organic compound, in order to increase their dispersibility. Preferably, this after-treatment is carried out with the same organic medium (complexing agent) which will be used in the shell synthesis or organic media of similar polarity.

If for instance the shell synthesis is to be carried out in N- or P-containing media, the after-treatment can suitably involve subjecting particles obtained in sol-gel processes, the glycothermal or hydrothermal synthesis or the so-called "polyol or sulfoxide synthesis" to an after-treatment with N- or P-containing media.

This after-treatment involves heating the nanoparticles in the corresponding organic compound. It has the effect that water, or other hydrophilic residues bonded at the surface of the nanoparticle are replaced by the polar organic compound. For the reasons given above, the polar organic compound is preferably selected from N- or P-containing complexing agents for metal ions as will be described further below in the context of the "organic synthesis" and the second process step. However, other functionalised polar organic compounds may also be used.

This after-treatment is not required for sulfates, as produced in the "polyol or sulfoxide" synthesis, if the subsequent manufacture steps are carried out in polyols and/or sulfoxides.

According to a further and preferred technique, hereinafter referred to as "organic synthesis", the process for the preparation of the nanoparticle cores comprises the steps of:

a) reacting, in an organic reaction medium comprising at least one metal complexing agent, and optionally at least one further solvent, a reaction medium-soluble or dispersible metal source and a reaction medium-soluble or -dispersible anion source, in particular phosphate, sulfate or fluoride source, b) optionally removing the reaction medium from the nanoparticulate metal salt (e.g. phosphate, sulfate or fluoride) formed thereby, and c) optionally recovering the nanoparticulate salt.

As "organic medium" we understand organic solvents, which, apart from unavoidable traces, do not contain water. The boiling point of this organic medium is preferably higher than the reaction temperatures given below. It is e.g. from 150 to 400° C., preferably above 180° C., in particular above 210° C. (at ambient pressure).

Depending on the susceptibility of the metal source to oxidation, it is preferred to conduct the reaction under inert gas such as nitrogen or argon.

Regarding the degree of purity of starting materials, it is recommendable to use metal salts having a purity of at least 99.9%. All reactants and the solvents used are preferably water-free and/or are dried prior to use. However, metal chlorides which are frequently employed as hydrates should preferably not be subjected to a longer drying procedure since this may enhance the formation of reaction medium-insoluble oxychlorides.

The reaction is preferably conducted at a temperature of 50 to 350° C., e.g. 120° to 320° C., in particular 180° to 290° C. A suitable temperature can be easily determined by a skilled person by monitoring the reaction of the reactants at gradually increasing temperatures thereby determining the synthesis minimum temperature at which the reaction proceeds with sufficient speed. For this purpose the nanoparticles may, for instance, be precipitated from samples of the reaction medium which allows studying the particle growth with increasing reaction time.

Suitable reaction times can be determined in the same manner and preferably range from 10 min to 48 hours, in particular 30 min to 20 hours.

After completion of the reaction, the reaction mixture can be cooled down to room temperature. If the nanoparticles have not yet fully precipitated during the reaction or after cooling, it is possible to add methanol to the reaction medium or vice versa in order to obtain maximum yields.

Without being bound to theory, it is believed that the metal complexing agent used in the "organic synthesis" coordinates with surface metal atoms of the nanoparticles formed and thereby terminates their growth after the starting materials have reacted. It is believed that this metal complexing agent remains bound to the particle surface and in this manner prevents or reduces agglomeration and exchange processes between the particles like Oswald ripening. The organic synthesis thus leads to fairly small particles wherein the average diameter measured at the longest axis is preferably 1-10 nm, in particular 2-8 nm, for instance 4-6 nm with narrow size distributions (standard deviation<30%, in particular <10%). The metal complexing agent is characterized by the presence of a polar group capable of coordinating the metal ion and at least one second molecule portion (less polar, preferably hydrophobic), for instance an aliphatic, aromatic/aliphatic, or purely aromatic molecule portion having preferably 4 to 20, in particular 6 to 14 carbon atoms.

The metal complexing agent is preferably a phosphororganic compound or a mono- or di-substituted amine.

Among the latter, the most preferred embodiments are mono- or dialkyl amines wherein the alkyl residue preferably has from 4 to 20, in particular 6 to 14 carbon atoms, such as dodecyl amine or bis(ethylhexyl)amine.

As regards the phosphororganic compounds, it is preferred to use at least one of the following substances:

a) esters of phosphinic acid

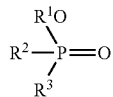

b) diesters of phosphonic acid

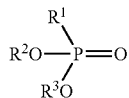

c) triesters of phosphoric acid, most preferably trialkyl phosphates such as tributylphosphate or tris(ethylhexyl)phosphate,

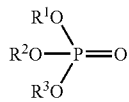

d) trialkyl phosphines, such as trioctylphosphine (TOP),

or e) trialkyl phosphine oxides, such as trioctylphosphine oxide (TOPO)

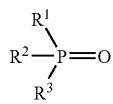

wherein $R^1$, $R^2$ and $R^3$ are independently selected from branched or linear aliphatic (preferably alkyl), aliphatic/aromatic or aromatic residues having from 4 to 20, more preferably from 4 to 14, in particular from 4 to 10 carbon atoms. Aromatic residues can be exemplified by phenyl and aliphatic/aromatic residues by tolyl, xylyl or benzyl.

The use of phosphororganic compounds (a) to (c) and (e), in particular (a) to (c) is particularly preferred.

The metal complexing agent can be the only solvent in the organic reaction medium. It is preferably used in an amount of at least 10 mol based on the molar amount of the metal atom(s) used as metal source, if it represents the only solvent. A preferred upper limit is approximately 1000 mol.

Depending on the choice of the metal complexing agent and, in particular, the length of the hydrophobic molecule portion, the use of larger amounts may be inconvenient as it can hamper a complete precipitation of the nanoparticles formed.

Therefore, it is preferred to use additionally "at least one further solvent". In this embodiment, the metal complexing agent ("first solvent") is preferably used in a molar amount of less than 10 mol, more preferably 0.9 to 6 mol, based on one mol of the metal ions (as used as metal source). The amount of the "further solvent(s)" is preferably from 5 to 100 mol, based on one mol of metal atoms (as used as metal source).

The "further solvent(s)" should be miscible with the metal complexing agent and have a boiling point above the synthesis minimum temperature, preferably a boiling point above 150° C., more preferably above 180° C., most preferably above 210° C. Boiling points above 400° C. can be undesired.

The "further solvent(s)" can be hydrocarbon-based or have at least one polar group. The use of the latter is preferred, if water of crystallization is present in the metal salt starting materials and said water is to be replaced by a solvent which is capable of coordinating to the metal. The "further solvent(s)" is (are) preferably selected from solvents having at least one ether functionality; in particular, dialkylethers having from 5 to 10 carbon atoms per alkyl group, such as dipentyl ether, dihexyl ether, diheptyl ether, dioctyl ether, or diisoamyl ether; diaryl ether or diaralkyl ether, having in total from 12 to 18 carbon atoms, such as diphenyl ether or dibenzylether; or mono- or polyethyleneglycol (PEG) dialkylether (wherein each alkyl preferably has from 1 to 4 carbon atoms and the average number of PEG units preferably is up to 10), such as diethyleneglycol dibutyl ether, triethyleneglycol dibutyl ether, and/or tetraethyleneglycol dimethylether;

branched or unbranched alkanes which preferably have from 10 to 18 carbon atoms, in particular 12 to 16 carbon atoms, such as dodecane or hexadecane; and/or organic high boiling base, preferably N-containing aliphatic base, most preferably a tri-substituted amine, in particular trialkylamine compounds having from 5 to 10 carbon atoms per alkyl group, such as trioctylamine or tris(2-ethylhexyl)amine or a N-containing aromatic base having preferably from 3 to 20 carbon atoms, such as imidazol.

These solvents may also be used in combination. The organic high-boiling base may not only serve as solvent, but can also function as acid scavenger. For instance if an acid, such as phosphoric acid or HF is employed as anion source, then it is preferred to use the base in an approximately equimolar amount (e.g. about 0.6 to 1.4 mol) with respect to the hydrogen(s) atom(s) of the acid.

"cation source" can be selected from any suitable (sufficiently reactive) metal salt and is preferably a metal chloride, metal alkoxide (wherein the alkoxide preferably has from 1 to 6 carbon atoms, in particular from 1 to 4 carbon atoms), a metal nitrate or metal acetate. The use of metal chlorides is particularly preferred. Hydrated metal salts may also be used. However, it is preferred to remove the crystallization water before the reaction.

"anion source" is preferably selected from starting materials disclosed in PCT/DE 01/03433. For the synthesis of nanoparticulate sulfates, phosphates, borates, fluorides, sulfides, arsenates or silicates, the following compounds are suitable:

a. sulfuric acid, phosphoric acid, boric acid or HF,
b. sulfide, arsenate, phosphate, borate, sulfate, silicate or fluoride salts that are soluble or at least dispersible in the synthesis mixture, in particular salts having an organic cation or alkali metal salts, or
c. esters which decompose at higher temperatures, such as boric acid alkyl esters, sulphuric acid alkyl esters, arsenic acid alkylesters or silicic acid alkyl esters (e.g. tetraethyl orthosilicate)

As to option b, the cation is preferably selected from basic N-containing aliphatic, aromatic and aliphatic/aromatic substances which preferably have from 4 to 30, preferably from 4 to 20 carbon atoms. Suitable cations involve, for instance, quaternary ammonium or phosphonium as described above or protonated aromatic bases, such as pyridine or collidine. For the preparation of phosphate nanoparticles, tetrabutylammonium dihydrogenphosphate, tetramethylammonium dihydrogenphosphate, or triethylammonium dihydrogenphosphate may be used as anion source. Correspondingly, sulfate nanoparticles can be produced from starting materials such as tetrabutylammonium hydrogensulfate, tetramethylammonium hydrogensulfate, bis-tetrabutylammonium sulfate, or triethylammonium hydrogensulfate. For the preparation of nanoparticles with fluorine-containing anions, triethylamine-trihydrofluoride, tetrabutyl ammonium fluoride, tetrabutyl ammonium hydrogendifluoride, dodecylamine hydrofluoride or the less soluble pyridine hydrofluoride, or collidine hydrofluoride can be used.

If the metal ion (cation source) dissolves too slowly in the organic medium, it is preferred to dissolve the same in a lower alcohol, preferably methanol, prior to the addition of the metal-complexing agent and reaction solvent. Methanol and water of crystallization are then removed by distillation and drying, before further reactants are added.

According to the claimed process, nanoparticles obtainable according to one of the above synthesis techniques are provided as dispersion in an organic medium (so-called "first mixture")

The organic medium is preferably based on one or more polar solvents having a boiling point of more than 120° C., in particular more than 180° C., but less than 400° C. It is preferably selected from "metal-complexing agents", in particular said mono- or dialkyl amines wherein the alkyl residues have from 4 to 20 C atoms, phosphororganic compounds, polyols and sulfoxides. Preferably, the organic medium contains the metal-complexing agent and optionally "at least one further solvent" described in the context of the organic synthesis.

Correspondingly, it is possible and preferred to employ nanoparticles produced in an "organic" synthesis or "polyol or sulfoxide" in the first step of the claimed process without isolating the same.

It should be noted that the organic medium serves as a dispersion medium for the nanoparticle cores. Thus, due to the ability of the organic medium to coordinate to the metal atom, the nanoparticles are maintained in their colloidal (non-dissolved) state before a shell can be grown thereon.

II.2. Second Process Step
In the second step
the above-described first mixture,
an anion source for the shell to be formed, in particular a phosphate, sulfate or fluoride source, and
a so called "second mixture", comprising shell-forming metal ions (and their counterion) and an organic complexing agent for said metal ions
are reacted at a temperature of 50 to 350° C. until a luminescent shell has formed around said nanoparticles.

Generally, it is preferred to keep anion source and first mixture separate in order to avoid a premature reaction.

The second process step can be conducted according: to the following three embodiments (A), (B) and (C):

Process (A) comprises the steps of
preparing a first mixture comprising metal salt or oxide nanoparticles, e.g. metal sulfate, phosphate or fluoride nanoparticles in an organic medium,
heating said first mixture to a temperature of 50 to 350° C.,
adding to this first mixture at this temperature, dropwise and separately, an anion source for the shell to be formed and a second mixture comprising shell-forming metal ions and an organic complexing agent for said metal ions, and
reacting the resulting mixture at this temperature until a luminescent shell has formed around said nanoparticles.

The separate, but simultaneous addition of anion source and second mixture, for instance by means of two dropping tunnels reduces the concentration of active starting materials for the shell and thus increases the selectivity of the reaction by decreasing independent particle growth from the starting materials for the shell.

Process (B) comprises the steps of
preparing a first mixture comprising nanoparticles of a first metal salt or oxide, e.g metal sulfate, phosphate or fluoride nanoparticles in an organic medium,
adding a shell-forming anion source to said first mixture
heating the resulting mixture to a temperature of 50 to 350° C.,
adding dropwise thereto a second mixture comprising shell-forming metal ions and an organic complexing agent for said metal ions, and
reacting the resulting mixture at this temperature until a luminescent shell has formed around said nanoparticles.

Process (A) and (B) tend to form more uniform particles, which further contain a smaller percentage of independently grown particles of shell-forming material.

Process (C) comprises the steps of
preparing a first mixture comprising nanoparticles of a first metal salt or oxide, e.g. metal sulfate, phosphate or fluoride nanoparticles in an organic medium,
combining said first mixture, an anion source for the shell to be formed and a second mixture comprising shell-forming metal ions and an organic complexing agent for said metal ions, preferably by adding said first mixture and said anion source to said second mixture, and
heating the resulting mixture to a temperature of 50 to 350° C. until a luminescent shell has formed around said nanoparticles.

Surprisingly, it was found that a gradual-addition, e.g. dropwise, of starting materials is not absolutely required. Although, according to process (C), the starting materials can be combined by mixing the complete portions, the desired core/shell material is formed with high selectivity and little independent particle growth. Process (C) thus is more easily handled than processes (A) and (B).

If not stated otherwise, the following preferred embodiments apply to all three processes (A), (B) and (C).

As metal ion source any sufficiently reactive metal salt can be used, preferably chlorides or alkoxides of the shell metal ion. The alkoxide group preferably has from 1 to 4 carbon atoms.

Any suitable anion source can be used as long as it is capable of forming a shell around the core particles provided in the first step.

Suitable anions forming the shell involve, but are not limited to phosphates, halophosphates, arsenates, sulfates, borates, aluminates, gallates, silikates, germanates, oxides, vanadates, niobates, tantalates, tungstates, molybdates, alkalihalogenates, other halides, nitrides, sulfides, selenides, sulfoselenides oder oxysulfides.

It is preferred to use for the shell formation anions which suitably react in organic media under similar or identical conditions as described in PCT/DE 01/03433. Examples involve silicates, borates, arsenates, sulfides, sulfates, phosphates, and fluorides, in particular sulfates, phosphates and fluorides. This document also teaches which anion sources can be used for generating the corresponding nanoparticulate material.

As to a suitable silicate, borate, arsenate, sulfide, sulfate, phosphate and fluoride source, reference is also made to anion sources described above for the first step of the claimed process, in particular those employed in the "polyol or sulfoxide" and/or "organic" synthesis.

The anion source is preferably added as fine dispersion or solution in at least one of the solvents described for the "polyol or sulfoxide" or "organic" synthesis.

The anion source, in particular phosphate, fluoride or sulfate source is preferably used in amounts of 0.75 to 3 mol, in particular 0.75 to 2, based on the stoichometrically required molar amount for reacting with all shell-forming metal atoms added. With binary salts (AB) the ratio B (anion) to A (metal) thus ranges thus from 0.75:1 to 2:1.

Phosphate and Fluoride sources, such as phosphoric acid or HF are preferably employed in excess amounts in the "organic" synthesis of core or core/shell particles made from phosphate or fluoride. The excess molar amount is preferably at least 1.05 mol, more preferably 1.1 to 2 mol, in particular 1.2 to 1.6 mol based on the stoichometrically required molar amount.

It is similarly preferred to use sulfate sources, such as quaternary ammonium (hydrogene)sulfate salts in excess amounts in the "polyol or sulfoxide" synthesis of sulfate core or core/shell particles. The excess molar amount is preferably at least 1.05 mol, more preferably 1.1 to 3 mol, in particular 1.2 to 2 mol based on the stoichometrically required molar amount.

The organic complexing agent contained in the second mixture may also be selected from the organic complexing agents explained above in the context of the organic synthesis of nanoparticles or the solvents described for the "polyol or sulfoxide synthesis".

Generally, it is desirable to keep the effective concentration of the shell-forming ions as low as possible. In accordance with the present invention, this is achieved by the use of this metal complexing agent. Without being bound to theory, it is believed that only a small concentration of reactive (uncomplexed) metal ions favors shell growth vis-à-vis the independent formation of new particles.

According to a preferred embodiment, the organic medium used for the first mixture and the complexing agent being present in the second mixture represent one of the phosphororganic compounds, mono/di-substituted amines, polyols or sulfoxides mentioned before. It is further preferred to use the same polar organic compound as organic medium and complexing agent.

Moreover, it is preferred to use the aforementioned "at least one further solvent" in the same ratio to the organic complexing agent. This allows using lower amounts of metal complexing agent as if it constitutes the only solvent. Then the molar ratio of metal complexing agent and shell-forming metal ions is again preferably 0.9:1 to 6:1.

If the anion source for the shell material possesses acid hydrogen atoms, it is preferred to use the above-described bases. The above-described organic high-boiling base (e.g. trialkylamine) is for instance preferably used as acid scavenger for anion sources like phosphoric acid or HF under the conditions described. This organic high-boiling base may also be added in the synthesis of silicates, borates, arsenates, or sulfates, typically if anion sources having acid hydrogen atoms are employed. According to process (A) or (B), the base is preferably added as ingredient of the "second mixture" comprising the metal source and complexing agent.

The total amount of solvent(s), including the metal complexing agent can be easily determined by a skilled person, since it is generally preferred to dissolve or disperse all starting materials homogeneously. In-process (A) and (B) it is preferred to use approximately the same amounts of solvents for dissolving the anion source and the metal source (second mixture).

Generally speaking, the reaction preferably proceeds under the same or similar conditions as discussed before under Item II.1 for the "polyol or sulfoxide" or "organic" synthesis, if not stated otherwise. This also applies to the use of protecting inert gas and the drying of the reactants.

The amount of nanoparticle cores to be combined with the remaining starting materials is not specifically limited and primarily depends from the targeted shell thickness.

According to the process of the present invention, the reaction medium is heated to a temperature of from 50 to 350° C., in particular 120° to 320° C. until a luminescent shell has formed around the nanoparticle cores prepared in the first process step.

The reaction is preferably conducted at a temperature of from 160° to 240° C., in particular 180° to 220° C. for the fluorides and phosphates, and 160° to 180° C. for the sulfates. The formation of sulfate shells in glycerol may also allow much lower temperatures (e.g., 50 to 100° C.). A suitable temperature can be easily determined by a skilled person by monitoring the shell growth at gradually increasing temperatures, thereby determining the synthesis minimum temperature at which the reaction proceeds with sufficient speed, but without undesired side reactions, like the development of new particles from the starting materials employed for the shell.

In those processes (A and B) where starting materials are added dropwise, the addition time ranges preferably from 0.5 to 10 hours, in particular 1 to 5 hours.

Preferred reaction times range from 30 min to 48 hours, in particular from 1 hour to 20 hours, specifically from 1.5 to 16 hours. Again, monitoring the reaction, for instance by precipitating the nanoparticles from samples taken from the reaction medium and studying the particle size distribution in TEM micrographs, allows determining a suitable reaction time. The reaction must be terminated, for instance by cooling, as soon as Oswald ripening is observed, i.e. when the bigger particles start to grow at the expense of the smaller particles.

After completion of the reaction, the reaction medium is cooled down to room temperature. This already enhances the precipitation of the core/shell nanoparticles formed. If the precipitation is incomplete, the addition of precipitating solvents (e.g. methanol) to the reaction medium or vice versa allows a complete recovery of the reaction product. Alternatively, it is possible to distill off the excess of organic solvents, including the organic complexing agent or conduct an ultrafiltration through membranes with a preferred pore size corresponding to Dalton values in the order of 5000 to 10000. These values correspond to a cut-off of about 3 nm which is many cases great enough to allow the solvent passing and small enough to prevent the penetration and loss of nanoparticles. Typically, a pressure of 2 to 5 bar is necessary for exchanging the solvents in the corresponding ultra-filtration cells.

Further, it is preferred to wash the nanoparticles obtained, for instance with methanol, ethanol or isopropanol.

As regards shell materials from oxides, the synthesis of fluorescent, doped metal oxides, is for instance described in U.S. Pat. No. 6,309,701, including host metal oxide such as $Y_2O_3$, $ZrO_2$, CuO, $CuO_2$, $Gd_2O_3$, $Pr_2O_3$, $La_2O_3$, and mixed oxides, being doped with at least one rare earth metal (to be understood as Sc, Y, La and the elements 58 to 71), in particular Eu, Ce, Nd, Sm, Tb, Gd, Ho, and/or Tm.

In the manners indicated below and in the examples, it can be confirmed that shell growth actually has taken place.

One option involves the continuous monitoring of the reaction by precipitating small samples and analysing their particle size distribution, for instance in TEM micrographs. The samples drawn in this manner will show whether shell growth has occurred over the entire reaction time or the independent formation of smaller particles can also be observed. EDX analysis (energy-dispersive X-ray analysis) can prove the total composition of the nanoparticles. XPS spectroscopy may furnish additional information regarding the distribution of the composition from the outer to the inner portions of the particles, if the XPS is performed at different excitation energies. Moreover, the luminescence spectra of core/shell particles can often be easily distinguished from the core nanoparticles employed in the reaction as also shown in the examples.

III. Use of Core/Shell Particles

III.1 Use in Bioassays

The core/shell particles of the present invention can be advantageously employed in bioassays utilizing the luminescence properties thereof. A particularly interesting application for the present core/shell particles are (F)RET-based assays ("(fluorescence) resonance energy transfer" as explained above).

In biological systems (F)RET is often used to determine the spatial vicinity of correspondingly labeled biomolecules or molecule groups. The method can serve as proof for various biological reactions or interactions of interest, e.g. protein-protein interactions, antigen-antibody reactions during immunoreactions, receptor-ligand interactions, hybridism of nucleic acid or the binding of proteins to nucleic acids.

The determination that (F)RET occurred proceeds via measuring a change of intensity or a spectral change of donor or acceptor luminescence, or via measuring changes in the decay time of the donor luminescence.

Many applications of these techniques are described in the literature and are also applicable to the present invention which is not restricted in this respect: the determination of specific antigens in immunofluorescence assays (U.S. Pat. No. 3,996,345; U.S. Pat. No. 4,160,016; U.S. Pat. No. 4,174,384; U.S. Pat. No. 4,199,559), the determination of electrostatic potentials in specific localized areas on the surface of proteins (Yamamoto et al., *J. Mol. Biol.* 241, 1994, pages 714-731) or high-throughput screening processes (Boisclair et al., *J. of Biomolecular Screening* 5, 2000, pages 319-328).

Moreover, (F)RET systems can also determine the absolute distance between two biomolecules or within portions of one biomolecule, respectively. This technique has already been successfully applied to the protein or DNA structure analysis (Heyduk et al., *SPIE*, Vol. 3256, 1998, pages 218-222), the measurement of distances within polypeptides (Lakowicz et al., *Biophys. Chem.* 36, 1990, pages 99-115), proteins (K. Cai et al., *J. Biol. Chem.* 271, 1996, pages 27311-27320), polynucleotides (Hochstrasser et al., *Biophys. Chem.* 45, 1992, pages 133-141 and Ozaki et al., *Nucl. Acids Res.* 20, 1992, pages 5205-5214) or other macromolecules, the analysis of membranes and membrane proteins and their construction (S. Wang et al., *Biochemistry* 27, 1988, pages 2033-2039), the detection (U.S. Pat. No. 4,996,143; U.S. Pat. No. 5,532,129; U.S. Pat. No. 5,565,332) and quantification of amplified nucleic acids by PCR (Polymerase Chain Reaction) (U.S. Pat. No. 5,538,848; U.S. Pat. No. 5,723,591), for example, for in vitro diagnostics, genetic analysis, forensic analysis, food and agrochemical tests or parentage tests. The DNA or RNA is directly, i.e. without additional separation steps, detected or quantified.

A quantitative nucleic acid determination by real time PCR with (F)RET systems is the as TaqMan® assay (Applied Biosystems Division of Perkin-Elmer Corp., Foster City, USA) known 5'-nuclease assay (U.S. Pat. No. 5,538,848; U.S. Pat. No. 5,210,015; Holland et al., *Proc. Natl. Acad. Sci. USA* 88, 1991, pages 7276-7280; Lee et al., *Nucleic Acids Res.* 21, 1993, pages 3761-3766). The method of molecular beacons (Tyagi and Kramer, *Nature Biotechnology* 14, 1996, pages 303-306; U.S. Pat. No. 5,312,728) is based on a similar mechanism.

Recently a review on "FRET in biochemistry" was published by S. Brakmann and N. Nöbel in *Nachrichten aus der Chemie*, 51, March 2003, pages 319-322, who describe further alternatives for FRET-based bioassays where the core/shell particles of the present invention can also be employed.

Accordingly, the core/shell particles of the present invention can be used in (F)RET-based bioassays, comprising a first molecule group A which is labeled with at least one energy donor (donor) and at least a second molecule group B which is labeled with at least one energy acceptor (acceptor), wherein the donor comprises a molecule or particle, which can be energetically excited by an outer radiation source and is capable of emitting luminescence, and the acceptor comprises a molecule or particle, which can be excited by energy transfer from the donor under partial or complete quenching of the donor luminescence, and donor and/or acceptor comprise the core/shell particles of the present invention, preferably those having an average diameter measured along their longest axis of not more than 50 nm, in particular not more then 30 nm, etc. as described hereinbefore.

This assay can be conducted in two manners. (F)RET-based assays require that the acceptor is also capable of emitting luminescence. RET systems function also if the acceptor relaxes without emitting radiation.

Preferably, the core/shell particles of the present invention are used as donor. Since these emit electromagnetic radiation with stokes or anti-stokes shift after energetic excitation, a spectroscopic distinction between excitation source and emitted radiation is easily possible.

The core/shell particles of the present invention show a superior behavior in bioassays of the above type since their luminescence can be more effectively quenched. Without wishing to be bound to theory, it is believed that the higher percentage of luminescent centers located at or in close vicinity to the surface as compared to homogeneous particles accounts for this observation. The higher susceptibility to quenching brings about various important advantages in (F)RET-based bioassays, such as a higher sensitivity.

The higher susceptibility to quenching can be noted in the decay curves (intensity of luminescence versus time) as shorter half values (half life) of the donor. In time-gated fluorescence spectroscopy (TGF modus) an almost complete disappearance of donor luminescence (core/shell particles) is obtained due to a very efficient energy transfer to the acceptor system, as explained in further detail in the examples.

As regards preferred embodiments of the core/shell particles to be used as donor and/or acceptor, preferably only as donor, reference is made to Item I of the specification.

When selecting a suitable donor/acceptor pair, it is generally recommendable to employ donor probes having a high quantum yield. Further, it is required that the emission spectrum of the donor probe must overlap considerably with the absorption spectrum of the acceptor probe. A further requirement, the appropriate alignment (approximately parallel) of donor and acceptor transition dipole orientations, is generally not a problem in biological systems allowing unrestricted isotropic motion of donor and acceptor. Further, as already mentioned, the Förster distance is to be taken into account insofar as donor and acceptor are preferably within $1\pm0.5\, R_0$ (Förster distance) from each other. The Förster distance is the distance at which energy transfer is 50% efficient. It can be calculated, as known in the art, from the spectral properties of donor and acceptor.

Typical donor and/or acceptor systems other than the core/shell particles of the present invention are organic dyes such as-fluorescein, tetramethylrhodamine, IAEDANS, EDANS, Dabcyl, BODIPY FL, QSY 7 and QSY 9. Other commercially available luminescent organic dyes being suitable for the spectral range of about 350 to 750 nm and above involve Alexa Fluor dyes (manufactured by Molecular Probes) or CyDyes (Amersham Pharmacia). Among these dyes, those absorbing and emitting at higher wavelengths (visible to near IR) are particularly attractive since they do not damage biological systems.

According to the present invention it is preferred to use the core/shell particles of the present invention as donor in combination with a suitable acceptor selected from the above organic fluorescent dyes.

Particles having a $Eu^{3+}$-doped shell can, for instance, be combined as donor with Alexa Fluor 680 as acceptor, or $Tb^{3+}$-containing particles with Dabcyl or Fluorescein. Examples for these Tb-containing core/shell particles are, for instance, core/shell systems having an inert (non-luminescent) core surrounded by a $Tb^{3+}$- or $Ce^{3+}$, $Tb^{3+}$-doped metal salt or oxide as shell, as well as core/shell systems based on a Cerium ($Ce^{3+}$) salt or oxide core surrounded by a Terbium ($Tb^{3+}$) salt or oxide shell.

Core/shell particles having an average diameter below 50 nm show a smaller potential for undesired steric interactions or sedimentation in bioassays than bigger particles. Moreover, less impact on the kinetics of the binding reaction (for instance, immunoreaction or DNA hybridization) of the biochemical process to be examined is to be expected.

Two different spectroscopic modes are typically applied for measuring the energy transfer in (F)RET-based systems (WO 87/07955; EP 242 527; EP 439 036; WO 92/01225; U.S. Pat. No. 4,822,733; U.S. Pat. No. 5,279,943; U.S. Pat. No. 5,622,821; U.S. Pat. No. 5,656,433; U.S. Pat. No. 5,998,146; U.S. Pat. No. 6,239,271), i.e. time-gated fluorometry (TGF) and/or time resolved fluorometry (TRF). According to TGF mode, the fluorescent donor is excited with a pulsed light source (e.g., laser, flashlight), followed by measuring the light emission after a predetermined delay within a specific time window. The relatively short delay still allows measuring with sufficient high intensity the long-lasting luminescence of lanthanide ions. The relatively short-lasting background fluorescence (typically smaller than 1 μs) as caused by intrinsic autofluorescence of biological material, impurities of solvents or surrounding biological material is almost fully discriminated by the delay.

In contrast to the TGF mode, the TRF mode measures luminescence as a function of time at a constant wavelength. The donor is also excited by a pulsed light source or light sources modulated in a different manner.

Core/shell particles having a diameter of not more than 50 nm can be suitably used in TRF mode since for bigger particles, a major part of the particle volume is not close enough to the acceptor to participate in the energy transfer, thereby lowering the intensity of the effect.

According to the present invention, at least one of the (F)RET partners, i.e. donor or acceptor, shows a relatively long luminescence decay time whereas the other (F)RET partner is characterized by short decay times.

Preferably, core/shell particles having luminescence half values ranging from 1 microsecond to 50 milliseconds, more preferably between 100 microseconds and 10 milliseconds, are used as donor.

If these donors are combined with conventional organic fluorescence dyes which typically have shorter decay times, the donor sensitizes and prolongs the luminescence of the acceptor beyond its intrinsic luminescence. Measuring such systems in TGF mode allows excluding the short-lasting intrinsic acceptor luminescence and determining the sensitized acceptor luminescence with high sensitivity.

Other suitable acceptors can be selected from electrically conducting materials, such as gold, silver, platinum, or conductive metal oxides, such as In—In oxide (ITO) or conductive polymers.

In order to bind the core/shell particles of the present invention to the biological molecule(s) on which the assay is based, the following techniques can be applied.

The binding can be generated by
chemically modifying the core/shell particles which typically involves the generation of "functional groups" on the surface, said functional groups being capable of binding to a biological molecule, and/or
linking the optionally chemically modified surface of the core/shell particle with covalently or non-covalently bonded so-called "linking molecules",
followed by reacting the biomolecule(s) with the particles obtained thereby.

The term "linking molecule" means a substance capable of linking with the core/shell particles of the invention and also capable of linking to an affinity molecule or a molecule or molecule portion competing for the same binding sites of the affinity molecule as the target molecule, e.g. an epitope.

The term "target molecule" means an entity or group, the presence or absence of which in a material such as a biological sample is to be ascertained by use of the core/shell particles of the invention.

The term "affinity molecule" means a biomolecule which will selectively bond to the target molecule (if present) in the material (e.g. biological material) being analysed.

The term "functional groups" as used hereinbefore is not restricted to reactive chemical groups forming covalent bonds, but also includes chemical groups leading to an ionic interaction or hydrogen bonds with the biomolecule(s). Moreover, it should be noted that a strict distinction between "functional groups" generated at the surface and linking molecules bearing "functional groups" is not possible, since sometimes the modification of the surface requires the reaction of smaller linking molecules such as ethylene glycol with the nanoparticle surface.

The functional groups or the linking molecules bearing them may be selected from amino groups, carbonic acid groups, thiols, thioethers, disulfides, guanidino, hydroxyl groups, amine groups, vicinal dioles, aldehydes, alpha-haloacetyl groups, mercury organyles, ester groups, acid halide, acid thioester, acid anhydride, isocyanates, isothiocyanates, sulfonic acid halides, imidoesters, diazoacetates, diazonium salts, 1,2-diketones, phosphonic acids, phosphoric acid esters, sulfonic acids, azolides, imidazoles, indoles, N-maleimides, alpha-beta-unsaturated carbonyl compounds, arylhalogenides or their derivatives.

Non-limiting examples for other linking molecules with higher molecular weights are nucleic acid molecules, polymers, copolymers, polymerizable coupling agents, silica, proteins, and chain-like molecules having a surface with the opposed polarity with respect to the core/shell particles. Nucleic acids can provide a link to affinity molecules containing themselves nucleic acid molecules, though with a complementary sequence with respect to the linking molecule.

As examples for polymerizable coupling agents, diacetylene, styrene butadiene, vinylacetate, acrylate, acrylamide, vinyl compounds, styrene, silicone oxide, boron oxide, phosphorous oxide, borates, pyrrole, polypyrrole and phosphates can be cited.

Linking techniques are described in further detail below:

1. The surface of the core/shell nanoparticles can be chemically modified, for instance by the binding of phosphonic acid derivatives having functional reactive groups. One example of these phosphonic acid or phosphonic acid ester derivates is imino-bis(methylenphosphono) carbonic acid which can be synthesized according to the "Mannich-Moedritzer" reaction (Moedritzer and Irani, J. Org. Chem, 1966, 31, 1603). This binding reaction can be performed with core/shell particles as directly obtained from the preparation process of the present invention or after a pre-treatment (for instance with trimethylsilyl bromide). In the first case the phophonic acid (ester) derivative may for instance displace components of the reaction medium which are still bound to the surface. This displacement can be enhanced at higher temperatures. Trimethylsilyl bromide, on the other hand, is believed to dealkylate alkyl group-containing phosphorous-based complexing agents as used in the process of the invention, thereby creating new binding sites for the phosphonic acid (ester) derivative. The phosphonic acid (ester) derivative, or linking molecules bound thereto, may display the same functional groups as given above.

2. A further example of the surface treatment of core/shell nanoparticles involves heating the particles in a diole such as ethylene glycol. It should be noted that this treatment may be redundant if the synthesis of the core/shell particles already proceeded in a diole. Under these circumstances the synthesis product directly obtained is likely to show the necessary functional groups. This treatment is however applicable to core/shell particles that were produced in the above described N- or P-containing complexing agents. If such core/shell particles are subjected to an after-treatment with ethylene glycol, ingredients of the reaction medium (e.g. complexing agent) still binding to the surface can be replaced by the diole and/or can be dialkylated. The treatment with dioles results in water-soluble particles. Analogously, primary alcohols having a second functional reactive group, as indicated above, can be used for the after-treatment. It is also possible to replace N-containing complexing agents still bound to the particle surface by primary amine derivatives having a second functional group selected from the above examples.

3. The surface of the core/shell particles of the present invention can also be coated with silica. Silica allows a relatively simple chemical conjugation of organic molecules since silica easily reacts with organic linkers, such as triethoxysilane or chlorosilane. The particle surface may also be coated by homo- or copolymers. Examples for polymerizable coupling agents are N-(3-aminopropyl)-3-mercaptobenzamidine, 3-(trimethoxysilyl)propylhydrazide and 3-trimethoxysilyl)propylmaleimide. Other examples of polymerizable coupling agents were already mentioned above. These coupling agents can be used singly or in combination depending on the type of copolymer to be generated as nanoparticle coating.

4. According to one further surface modification technique, core/shell particles containing oxidic transition metal compounds can be converted by chlorine gas or organic chlorination agents to the corresponding oxychlorides. These oxychlorides are capable of reacting with nucleophiles, such as hydroxy or amino groups as often found in biomolecules. This technique allows generating a direct conjugation with proteins, for instance-via the amino group of lysine side chains. The conjugation with proteins after surface modification with oxychlorides can also be effected by using a bi-functional linker, such as maleimidopropionic acid hydrazide.

5. For non-covalent linking techniques, chain-type molecules having a polarity or charge opposite to that of the core/shell particle surface are particularly suitable. Examples for linking molecules which can be non-covalently linked to core/shell nanoparticles involve anionic, cationic or zwitter-ionic surfactants, acid or basic proteins, polyamines, polyamides, polysulfone or polycarboxylic acid. The hydrophobic interaction between nanoparticle and amphiphilic reagent having a functional reactive group can generate the necessary link. In particular, chain-type molecules with amphiphilic character, such as phospholipids or derivatised polysaccharides, which can be crosslinked with each other, are useful. The absorption of these molecules on the surface of the core/shell particle can be achieved by coincubation. The binding between affinity molecule and core/shell particle can also be based on non-covalent, self-organising bonds. One example thereof involves simple detection probes with biotin as linking molecule and avidine- or strepdavidine-coupled affinity molecules.

Protocols for coupling reactions of functional groups to biological molecules can be found in the literature, for instance in "Bioconjugate Techniques" (Greg T. Hermanson, Academic Press 1996). The biological molecule, in particular affinity molecule can be coupled to the linking molecule, covalently or non-covalently, in line with standard procedures of organic chemistry such as oxidation, halogenation, alkylation, acylation, addition, substitution or amidation. These methods for coupling a biological molecule to the covalently or non-covalently bound linking molecule can be applied prior to the coupling of the linking molecule to the core/shell nanoparticle or thereafter. Further, it is possible, by means of incubation, to effect a direct binding of affinity molecules to correspondingly pre-treated core/shell nanoparticles (for instance by trimethylsilyl bromide), which display a modified surface due to this pre-treatment (for instance a higher charge or polar surface). The molecule groups A and B, which were labeled with a donor or acceptor, respectively, can represent a part of the same molecule and for instance be coupled to the same affinity molecule. A change in the spatial distance of these molecule groups may for instance be caused by a confirmation change or by a cleavage of the molecule. This confirmation change or cleavage of the molecule can be the result of an interaction between the affinity molecule and a target molecule.

Alternatively, the molecule groups A and B can be located on different molecules, said molecule groups A and B each being coupled to their own affinity molecules. A change in the spatial distance can be brought about by an interaction of the affinity molecules being allocated to molecule groups A and B with a joint target molecule or with each other. This interaction can be for instance an interaction between proteins, such as an immunoreaction of antigen and antibody, a hybridism of nucleic acids or the interaction between nucleic acids and proteins.

The bioassay can be for instance a homogeneous immunoassay for detecting an analyte in a body sample (for instance swab, sputum, organ punctate, biopsies, secretion, liquor, bile, blood, lymph, urine, feces). Homogeneous assays do not require washing or separation steps.

The bioassay using the core/shell particles of the present invention can also be a heterogeneous assay.

The analyte (as a rule the target molecule) to be detected in the assay can be for instance a monoclonal or polyclonal antibody, protein, peptide, oligonucleotide, nucleic acid, oligo- or polysaccharide, haptene or low molecular synthetic or natural antigen.

Similarly, non-limiting examples for affinity molecules are proteins, peptides, oligonucleotides, or other nucleic acid molecules or related species such as PNAs or morpholinos as well as oligo- or polysaccharides, haptenes such as biotin or digoxine or low molecular synthetic or natural antigenes or epitopes.

The assay can be used in solution as well as in solid phase-based or array-based systems wherein oligo- or polynucleotide chains or antibodies or antigens, respectively, are immobilised on a surface.

Assays using the core/shell particles of the present invention can be utilized in various manners.

According to one application type, the (F)RET partners are located on the same molecule, i.e. both (F)RET partners are bound via corresponding linking molecules (partially not shown) with the same affinity molecule (FIG. 6a, 6b, 7, 10 and 11). The binding of a target molecule to the affinity molecule induces a confirmation change of the affinity molecule, thereby leading to a change of the spatial position of the labels with respect to each other and thus a measurable difference in (F)RET.

Figure 8:
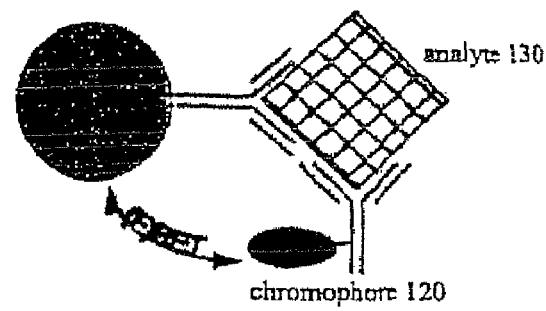
FIG. 8: Homogeneous saturation immunoassay with (F)RET partners coupled to separate molecules.
Figure 9:
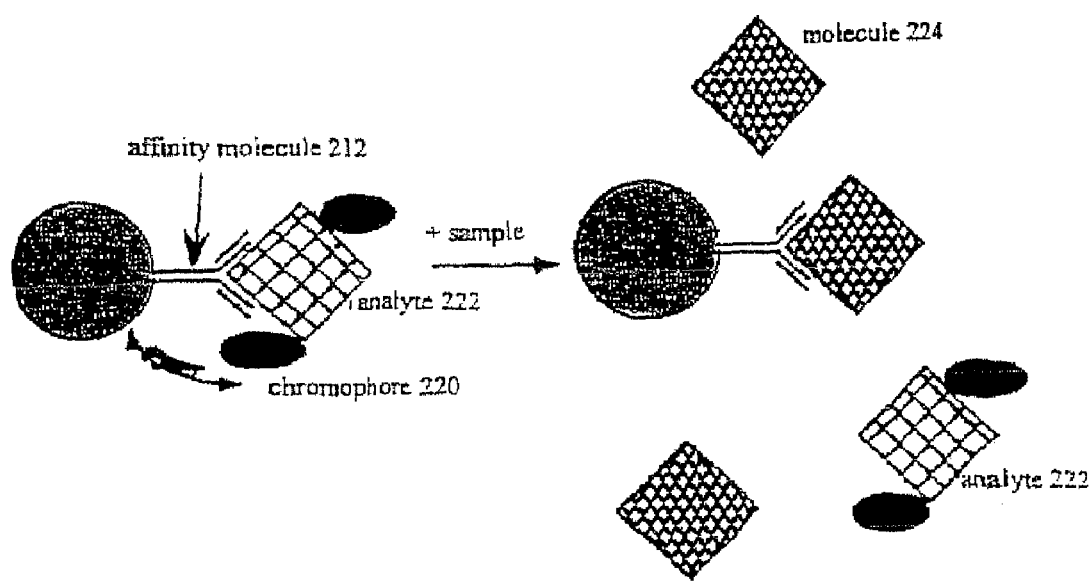
FIG. 9: Homogeneous competitive immunoassay with (F)RET partners coupled to separate molecules.

For other applications the (F)RET partners are located on different molecules and are each coupled to their own affinity molecule (FIG. 8) or the analyte and the affinity molecule (FIG. 9). The respective affinity molecules can be selected in a manner leading to an interaction between donor and acceptor which is produced or cancelled by the reaction with the target molecule, thereby inducing a change of energy transfer.

The use of core/shell nanoparticles according to the invention in (F)RET-based bioassays will now be further explained by means of the FIGS. 6 to 11.

Figure 6A:
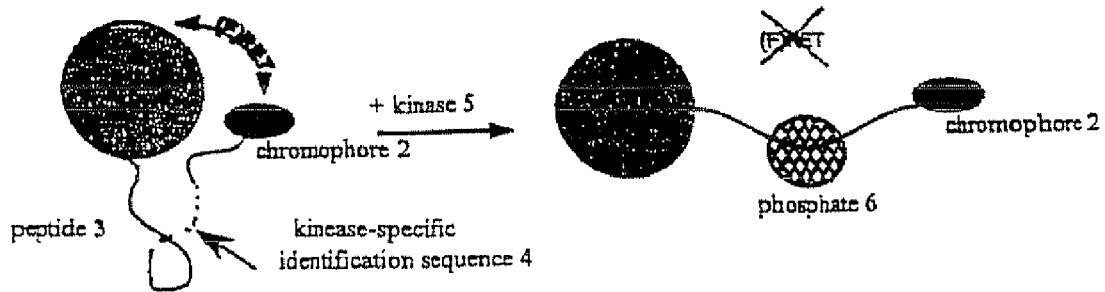
FIG. 6a: Homogeneous kinase assay with (F)RET partners coupled to one molecule

FIG. 6a shows schematically the interaction of (F)RET partners located on the same molecule in a homogeneous kinase assay. The lad-nanoparticle 1 (lad=luminescent anorganic doped) and chromophor 2 are linked by means of a peptide sequence 3. The peptide sequence contains a kinase-specific identification sequence 4. If the peptide sequence 3 is phosphorylated at this position by kinase 5, the presence of phosphate 6 changes the confirmation of the peptide sequence 3. Thus the interaction between the (F)RET partners, nanoparticle 1 and chromophore 2 becomes measurable.

Figure 6B:
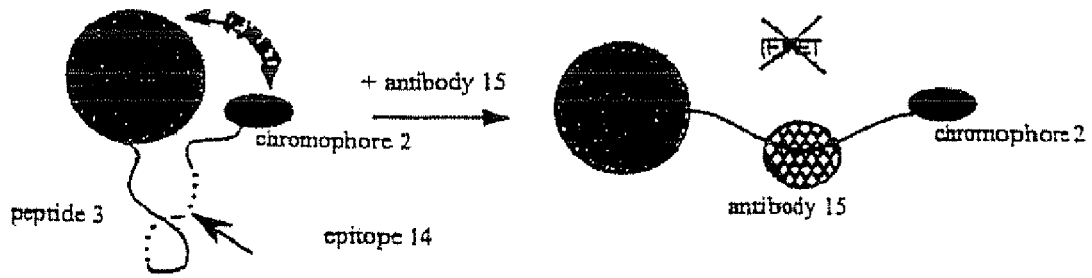
FIG. 6b: Homogeneous immunoassay with (F)RET partners coupled to one molecule.

FIG. 6b shows schematically a homogeneous immunoassay with (F)RET partners located on one molecule, for which protein-protein interactions are to be determined, for instance antigen-antibody reactions. Nanoparticle 1 and chromophore 2 are linked by means of peptide sequence 3. The peptide sequence contains epitope 14. If an antibody 15, which specifically recognizes epitope 14, binds to epitope 14, the confirmation of peptide sequence 3 is changed. Thereby the interaction between the (F)RET partners, nanoparticle 1 and chromophore 2, becomes measurable.

The molecule to be detected can directly bind to the affinity molecule as described in FIG. 6a and 6b. However, it may also be indirectly responsible for the binding of a molecule to the affinity molecule. One example of this is the measurement of $Ca^{2+}$ concentrations in living cells. For this purpose the calcium-dependent binding of calmoduline to myosin-light-chain kinase (MLCK) in unstriated muscles is utilized. The calmoduline binding domain of MLCK acts as affinity molecule and is coupled to (F)RET partners. Depending on the $Ca^{2+}$ concentration, calmoduline binds to the binding domain and effects a confirmation change of the detecting probe. This entails a change of the measurable (F)RET.

Figure 7:
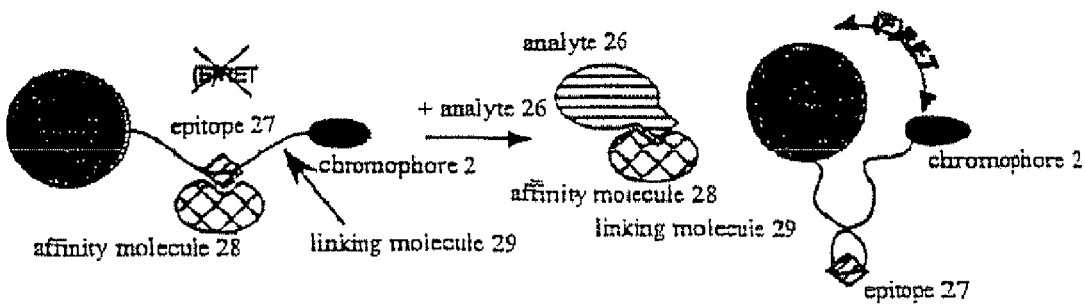
FIG. 7: Competitive immunoassay with (F)RET partners coupled to one molecule (epitope).

FIG. 7 shows schematically a competitive immunoassay with (F)RET partners located on one molecule which is used for determining the concentration of analyte 26 in a body sample. Nanoparticle 1 and chromophore 2 are linked by a linking molecule 29 which is bound to epitope 27. Epitope 27 is designed according to one epitope of the analyte 26 to be detected. The affinity molecule 28 binds specifically to epitope 27. By the addition of a sample (for instance a body sample) containing the analyte 26 to be detected, the affinity molecule 28 still being bound to the epitope 27 is displaced from this epitope 27. This results in a conformation change of affinity molecule 29 and thus in a measurable change of the interaction between the (F)RET partners, nanoparticle 1 and chromophore 2. This (F)RET change is utilized for determining the concentration of analyte 26.

FIG. 8 shows schematically a homogeneous saturation-immunoassay with (F)RET partners on different molecules. The affinity molecules of lad nanoparticle 110 and chromophore 120, respectively, can recognize different epitopes of the same target molecule 130, thereby leading to a measurable energy transfer in the presence of target molecule 130. One example of a homogeneous immunoassay where donor and acceptor are located on different molecules is the detection of hCG (human chorional gonadotropine) in serum. Therein donor and acceptor are coupled to antibodies that recognize different epitopes of hCG. If hCG is present in a body sample, donor and acceptor probes bind to the analyte. The measurable FRET can be used to determine the concentration of the analyte in the body sample by means of a calibration curve.

FIG. 9 shows schematically a homogeneous, competitive immunoassay with (F)RET partners 210 and 220 located on different molecules. One or more chromophores 220 are linked to molecule 222 which corresponds in part or completely to molecule 224 to be detected. The lad nanoparticle 210 is coupled to affinity molecule 212 which interacts specifically with molecule 222 and molecule 224 to be detected. A binding arises between affinity molecule 212 and molecule 222 thereby allowing (F)RET. If a sample (for instance a body sample) containing the molecule 224 to be detected is now added thereto, a displacement reaction occurs depending on the concentration of molecule 224 to be detected in said sample. This generates a measurable change, in this case a reduction of (F)RET, which allows determining the concentration of the molecule to be detected by means of a calibration curve.

Figure 10:
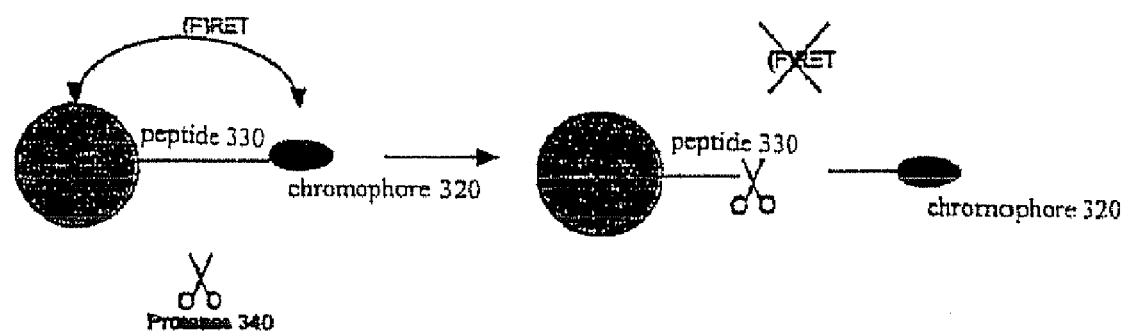
FIG. 10: Homogeneous assay with (F)RET partners coupled to one molecule.

FIG. 10 shows schematically a homogeneous assay with (F)RET partners located on one molecule. Lad nanoparticle 310 and chromophore 320 are linked by peptide 330 as affinity molecule. This peptide can be cleaved by enzyme 340 to be detected. After this cleavage (F)RET can no longer be observed.

The assay of FIG. 10 can be used for determining in a sample or cell a specific enzyme activity, for instance of a protease being specific for HI-virus. Both (F)RET partners are linked by the short identification sequence of this protease and will be separated spatially from each other by the activity of this protease leading to peptide cleavage. The enzyme activity to be detected may also stem from a restriction endonuclease. Then both (F)RET partners are linked by nucleic acid.

Figure 11:
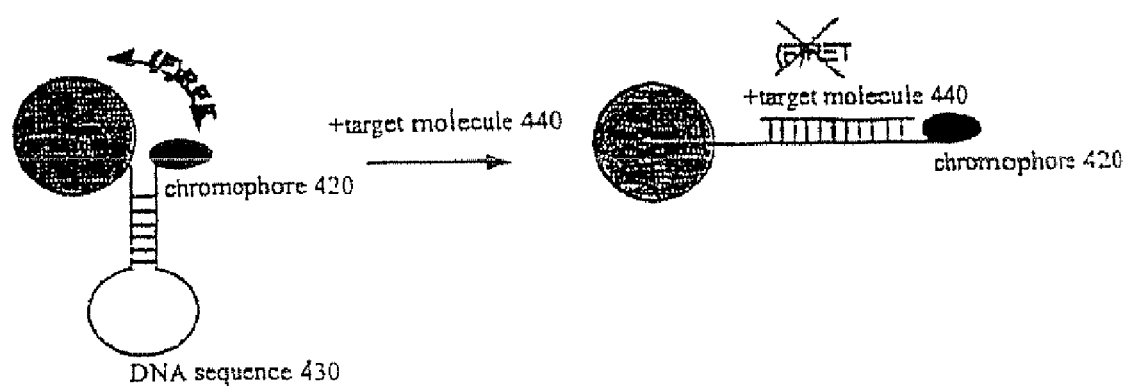
FIG. 11: Assay following the method of molecular beacons.

FIG. 11 shows schematically an assay following the method of molecular beacons. Molecular beacons are DNA molecules which are capable of folding themselves by intermolecular complementary sequences into a so-called stem-loop or hair-pin structure. One lad nanoparticle 410 is coupled to one terminus of DNA sequence 430. The other terminus binds to chromophore 420 as fluorescence cancellation agent or quencher. In the hair-pin structure both (F)RET partners 410 and 420 are arranged in close vicinity. The fluorescence of donor 410 is therefore fully quenched. The target molecule 440 shows sequences which are complementary to the loop region of DNA sequence 430. Since the binding of target molecule 440 is energetically more favourable, the hair-pin confirmation is dissolved, chromophore 420 and lad nanoparticle 410 separate from each other and measurable fluorescence is emitted since (F)RET does no longer cause fluorescence quenching. The hybridism properties can be adjusted in such a manner that one single base pair mismatching between molecular beacon 430 and target DNA 440 does not result in an opening of the hair-pin structure. Thus it is possible to detect even single base differences (for instance SNPs, single nucleotide polymorphisms).

This technique shown in FIG. 11 can also be used in brand protection and/or security marking of products. If a product is marked with DNA (fragments) showing at both ends short complementary structures whereof one is linked to a core/shell particle of the present invention and the other one to acceptors as explained above, (F)RET can be observed in the resulting molecular beacon (hair-pin structure). As soon as this DNA (fragment) is contacted with the complementary structure, hybridism will dissolve the hair-pin structure thereby preventing (F)RET. This allows a specific identification and protection of commercial products. Brand protection based on synthetic DNA identification is already commercialized, for instance by November AG, Germany.

III.2 Other Uses

Independently from their use in bioassays, the claimed core/shell particles generally allow the (F)RET-based measurement of nanometer distances in biological or other systems, if being combined with a suitable luminescence acceptor. Such measurements may for instance be of interest for spectroscopic purposes in nanomaterial sciences.

Moreover, the claimed core/shell particles can be used for various industrial devices and products demanding excellent (photo) luminescence properties.

For this purpose they are typically prepared as dispersion in fluid or solid media.

Suitable fluid media comprise for instance an organic or aqueous dispersion medium, a coating composition, an ink or dye, a polymer composition, or an aerosol. Suitable organic dispersion media involve, but are not limited to toluene, $CHCl_3$ or $CH_2Cl_2$.

The synthesis with N- or P-containing media/complexing agents, as described above ensures the ready dispersibility of the core/shell particles according to the present invention in organic media.

The preparation of an aqueous dispersion may require an after-treatment where residues of organic materials used in the synthesis are replaced by solvents having one functionality binding to the surface of the particles and one molecule portion ensuring the necessary compatibility in water, optionally in combination with water-miscible solvents.

The solid dispersion medium may be selected from a coating, ink or dye, a polymer composition, in particular a polymer film.

The nanoparticles as such, or typically a fluid or solid medium containing the same, can for instance be used for light generation, printing or marking items and materials.

Such applications are for instance light-emitting diodes, displays, optoelectronic devices, e.g. amplifiers with nm dimensions and light sources in zero-threshold lasers. They can also be used as ink in printing devices, which is of great interest in security marking of documents or money bills.

IV. EXAMPLES

Example 1

$CePO_4$ Nanoparticle Cores Having a $TbPO_4$ Shell

In a 100 ml round-bottom flask provided with a high performance reflux condenser, a temperature probe and heating mantel, 3.72 g (10 mmol) $CeCl_3 \times 7H_2O$ are dissolved in about 4 ml methanol followed by adding 40 ml tris-2-ethylhexylphosphat (TEHP) to the resulting solution. A vacuum is applied to the round-bottom flask in order to remove methanol and crystallization water, firstly at room temperature (1 to 2 hours) and then at 50° C. (about 1.5 hours).

In a second flask, dry ortho-phosphoric acid (20 mmol) is dissolved in 5 ml tetraethyleneglycoldimethylether.

Under a nitrogen atmosphere and at 50° C., 13.1 ml (30.0 mmol) trioctylamine and 2.5 ml ortho-phosphoric acid/tetraethyleneglycol dimethylether mixture are added to the $CeCl_3$ solution in TEHP. Thereafter the mixture is heated 15 hours to 200° C. After this period of time, a clear dispersion ("first mixture") of $CePO_4$ particles (average diameter 5 mm) is obtained.

In a second 100 ml round-bottom flask provided with a high performance reflux condenser, a temperature probe and a heating mantel, 3.72 g (10 mmol) $TbCl_3 \times 6H_2O$ are dissolved in about 4 ml methanol followed by adding 40 ml tris-2-ethylhexylphosphat (TEHP) to the solution. After applying vacuum to this round-bottom flask, methanol and crystallization water are firstly removed at room temperature (1 to 2 hours) and then at 50° C. (1.5 hours). Under a nitrogen atmosphere and at 50° C., 13.1 ml (30 mmol) trioctylamine and 2.5 ml (10 mmol phosphoric acid) ortho-phosphoric acid/tetraethyleneglycol dimethylether solution as well as 14 ml of the $CePO_4$ dispersion (cooled down to about 20-30° C.) are added to the $TbCl_3$ solution ("second mixture"), followed by heating to 200° C. over 12 hours. After cooling to room temperature, the reaction mixture is poured into methanol in order to precipitate the core/shell nanoparticles. The precipitate is centrifuged (at 5500 upm) and the resulting particles are washed with methanol and dried.

Figure 2:
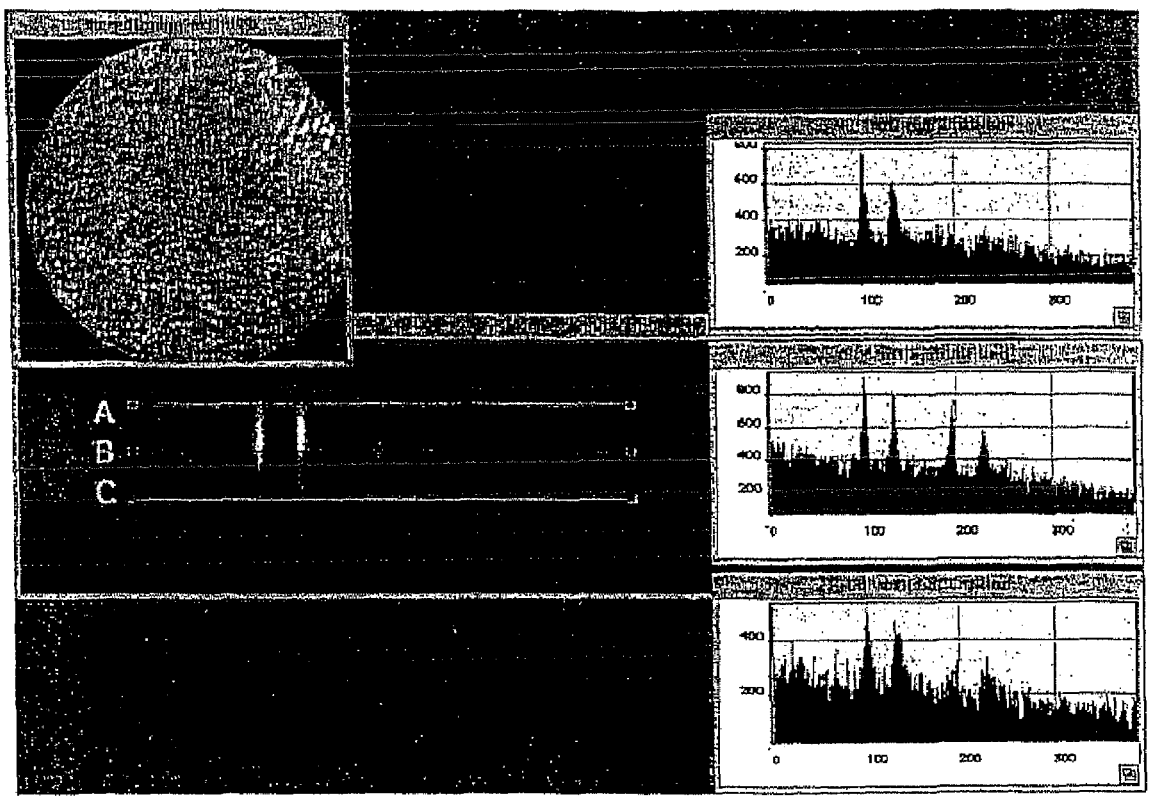
FIG. 2 shows various images obtained by energy filtering transmission electron microscopy of one $CePO_4$:Tb/$LaPO_4$ core/shell particle.

The photoluminescence spectrum of these particles as shown in FIG. 2 confirmed their core/shell structure.

TEM measurements further indicated that the particles had an average diameter (along their longest axis) of about 6 nm.

FIG. 1 shows the fluorescence spectra of homogeneous $CePO_4$ particles (line 1), and core/shell particles according to the present invention (lines 2 and 3) wherein a $TbPO_4$ shell grows around $CePO_4$ particles. The spectrum reflected by line 2 was taken after a reaction time of 0.5 hours whereas line 3 shows the fluorescence of $CePO_4$ cores having a fully developed $TbPO_4$ shell (reaction time 18 hours). The spectra were recorded at the same optical density ($10^{-3}$ wt-%) in i-propanol ($\lambda_{exc}$=274 nm).

As seen from FIG. 1, homogeneous $CePO_4$ particles are characterized by a strong fluorescence emission around 330 nm, but show no emission in the visible range. This situation dramatically changes by the $TbPO_4$ coating. $Ce^{3+}$ strongly absorbs the exciting irradiation, transfers the absorbed energy to $Tb^{3+}$ that emits the same in the form of four strong characteristic bands located at 488 nm, 545 nm, 586 nm and 617 nm. This energy transfer results in lowered Ce emission and strongly increases Tb emission.

Example 2

$LaPO_4$ Nanoparticle Cores Having a $TbPO_4$ Shell

In a 100 ml round-bottom flask provided with a high performance reflux condenser, a temperature probe and heating mantel, 3.2 g (8.6 mmol) $LaCl_3 \times 7H_2O$ are dissolved in about 10 ml methanol followed by adding 39 ml tris-2-ethylhexylphosphat (TEHP) to the resulting solution. A vacuum is applied to the round-bottom flask in order to remove methanol and crystallization water, firstly at room temperature (1 to 2 hours) and then at 50° C. (several hours).

In a second flask, dry ortho-phosphoric acid (20 mmol) is dissolved in 5 ml tetraethyleneglycol dimethylether.

Under a nitrogen atmosphere and at 50° C., 11.5 ml (26.3 mmol) trioctylamine and 2.3 ml ortho-phosphoric acid/tetraethyleneglycol dimethylether mixture are added to the $LaCl_3$ solution in TEHP. Thereafter the mixture is heated 16 hours to 200° C. After this period of time, a clear dispersion ("first mixture") of $LaPO_4$ particles is obtained.

In a second 100 ml round-bottom flask provided with a high performance reflux condenser, a temperature probe and a heating mantel, 2.97 g (8 mmol) $TbCl_3 \times 6H_2O$ are dissolved in about 10 ml methanol followed by adding 35.2 ml tris-2-ethylhexylphosphat (TEHP) to the solution. After applying vacuum to this round-bottom flask, methanol and crystallization water are firstly removed at room temperature (1 to 2 hours) and then at 50° C. (several hours). Under a nitrogen atmosphere and at 50° C., 10.5 ml (24 mmol) trioctylamine and 2.0 ml (8 mmol phosphoric acid) ortho-phosphoric acid/tetraethyleneglycol dimethylether solution as well as the entire amount of the $LaPO_4$ dispersion (cooled down to about 20-30° C.) are added to the $TbCl_3$ solution ("second mixture"), followed by heating to 200° C. over 16 hours. After cooling to room temperature, the reaction mixture is poured into methanol (300 ml) in order to precipitate the core/shell nanoparticles. The precipitate is centrifuged (at 5500 upm) and the resulting particles are washed twice with methanol and dried.

Reference Example 1

Analysis of Core/Shell Particle

The following reference example describes the measurement of chemical composition, core diameter and shell thickness of $CePO_4$:Tb nanoparticle cores having a $LaPO_4$ shell. Even though these particles are not covered by the claims, this analysis technique is fully applicable to the present invention.

For this purpose the particles were mounted on carbon film provided with holes and studied under a Philipps CM300UT microscope.

EELS (Electron Energy Loss Spectroscopy) showed that the average chemical composition of the cations was Ce/La=0.34±0.05, Tb/La=0.12±0.03 which means that La/Ce=3.0±0.4 and Ce/Tb=2.8±0.8, the latter value corresponding approximately to the molar ratio Ce/Tb (3.14/1) used.

HREM (High Resolution Electron microscopy) confirmed the crystallinity of the core/shell particles obtained.

Moreover, a Hellfeld image was taken with a slight underfocus at a scanning rate of 0.48 nm/image point in order to cover also smaller particles. The analysis of this image showed that the major particle class in terms of volume showed diameters from 5 to 9 nm. Six of this particles were subjected to EFTEM (Energy-filtering Transmission Electron Microscopy), specifically the so-called "spectrum image method" which was developed by the "Landeszentrum für Hochleistungsspektroskopie, Institut für Anorganische Chemie" in Bonn, Germany for quantitative analysis. For this purpose six crystalline particles were centered at very high magnification on the CCD camera behind the imaging energy filter. Then the smallest objective screen (4.6 mrad) and biggest entrance screen (3 mm) were inserted and the energy filter was used in its spectroscopy mode. Thereby the complete intensity passing the entrance screen is imaged line by line on the detector. Due to the chromatic aberration of the lense this process images only a section of about ±40 eV with high sharpness (below nm) so that it was focused on the $La_{M5,4}$ and $Ce_{M5,4}$ edges at 832, 849, 884 and 902 eV. At the selected primary magnification of 99K the diameter of the entrance screen was always 11.2 nm.

FIG. 2 shows (D) the Hellfeld image (with entrance screen) of one $CePO_4$:Tb nanoparticle surrounded by a $LaPO_4$ shell (diameter about 7 nm), (E) the spectrum image at 860 eV energy loss as well as profiles through the particle surface (A, C) and the center (B). The profiles (A, B and C) show the $La_{M5,4}$ and $Ce_{M5,4}$-peaks the relative intensity of which approximately corresponds to the local composition.

The different profiles confirm the existing core/shell structure of a core rich in Ce and a shell rich in La. The six selected particles had on average a diameter of 7.5±1.9 nm composed of a Ce-rich core having a diameter of 4.0±1.1 nm and a La-rich shell having a thickness of 1.9±0.7 nm (Tb was not determined in this analysis).

Example 3

Coupling of Fluorescein to Core/Shell Particles of Example 1 ($CePO_4$/$TbPO_4$)

3-1: Amino-functionalization of core ($CePO_4$)-shell ($TbPO_4$)-nanoparticles with imino-bis(methylenphosphono)-undecanoic acid and 1,4-bis(3-aminopropoxy)-butane 0.388 g (1 mmol) imino-bis(methylenphosphono)undecanoic acid are dissolved with 1.5 ml ethylene glycol and 0.51 g (2.5 mmol) 1,4-bis(3-aminopropoxy)-butane by heating to 50° C. for 30 min. The resulting solution is slightly yellowish. 25 mg (=71.5 nmol) of core ($CePO_4$)-shell ($TbPO_4$)-nanoparticles obtained in example 1 are added to the solution, stirred and heated to ~120° C. for 4 h. The dispersion is turbid and slightly yellow. After dialysis (dialysis tubing Spectra/Por, 5-6.000 MWCO, Spektrum, Netherlands) over night against 2×2 l 10 mM Na-carbonate buffer, pH 8.5, the particles precipitate.

3-2: Coupling of Fluorescein to Amino-Functionalized Core (CePO$_4$)-shell (TbPO$_4$)-nanoparticles 5 mg (25 nmol) of the amino-functionalized nanoparticles (described above) are centrifuged for 10 min at 5000 rpm and the pellet is resuspended in 500 µl 0.2 M Na-carbonate buffer pH 8.5 yielding a concentration of 10 mg/ml. FITC (fluorescein isothiocyanate) is dissolved in a 1:1 solution of DMF and 0.2m Na-carbonate buffer, pH 8.5 to a concentration of 5 mmol/ml. A 17-fold excess (87 µl=429 nmol) is added to the particles and the mixture incubated rotating at room temperature for 4.5 h. The unbound FITC is separated using a sephadex G-25 M PD 10 column (Amersham Bioscience) and 10 mM Na-carbonate buffer pH 8.5 as elution buffer. The eluted fraction of 3.9 ml contains fluorescein-coupled nanoparticles.

Comparative Example 1

Coupling of Fluorescein to Homogeneous LaPO$_4$:Ce,Tb Particles

CE1-1: Production of LaPO$_4$:Ce,Tb nanoparticles 300 ml TEHP (Tris(2-ethylhexyl)phosphate) were degassed in a dry nitrogen stream. Thereafter, 7.43 g LaCl$_3$× 7H$_2$O (20 mmol), 8.38 g CeCl$_3$×7H$_2$O (22.5 mmol), and 2.8 g TbCl$_3$×6H$_2$O (7.5 mmol) are dissolved in 100 ml methanol and added to the TEHP. Then water and methanol are removed under vacuum at a temperature of 30 to 40° C. Then a freshly prepared solution of 4.9 g dry orthophosphoric acid (50 mmol) dissolved in a mixture of 66.5 ml trioctylamine and 150 ml TEHP is added. The clear solution obtained is immediately placed under vacuum and purged with nitrogen in order to minimize the oxidation of Ce$^{3+}$ when raising the temperature. Thereafter the solution is heated to 200° C. The heating phase is terminated if the boiling temperature has decreased to 175° C. (after about 30 to 40 hours). After cooling to room temperature, a 4-fold excess of methanol is added to precipitate the particles. The particles are separated, washed with methanol and dried.

CE1-2: Dealkylation with Bromotrimethylsilane 300 mg of the LaPO$_4$:Ce,Tb-Nanoparticles (about 850 nmol) obtained in CE1-1 are refluxed over 4 hours with 2.3 g bromotrimethylsilane (15 mmol) in 100 ml chloroform. The majority of bromotrimethylsilane excess and volatile intermediate products are removed and separated under vacuum. The nanoparticle-containing residue is hydrolyzed over night under stirring in a mixture of 6 ml water and 100 µl ammonia (25%). The resulting particles form a milky suspension and sediment partially after several hours. They can be separated by centrifugation.

CE1-3: Aminofunctionalization of dialkylated LaPO$_4$:Ce,Tb nanoparticles with imino-bis (methylenphosphono)caproic acid 0.5 g (1.75 mmol) imino-bis(methylenphosphono)caproic acid (KBD9267) are dissolved with 0.894 g (4.375 mmol) 1,4-Bis(3-aminopropyl)-butane (Fluka) in 2 ml ethylene glycol by heating to 50° C. for 30 min The resulting solution is slightly yellowish. 35 mg (=175 nmol) of LaPO$_4$:Ce,Tb-nanoparticles obtained in CE1-2 are added to the solution, stirred and heated to ~120° C. for 4 h. The dispersion is clear and brownish also after cooling to room temperature. After dialysis against 2×2 l 10 mM Na-carbonate buffer, pH 8.5, the solution is slightly yellow and clear.

CE1-4: Coupling of Fluorescein to Amino-Functionalized LaPO$_4$:Ce,Tb Nanoparticles The solution of aminofunctionalized LaPO$_4$:Ce,Tb nanoparticles of CE1-3 is concentrated in vacuum to ~4.8 mg/ml. FITC (fluorescein isothiocyanate) is dissolved in a 1:1 solution of DMF and 0.2m Na-carbonate buffer, pH 8.5 to a concentration of 5 mmol/ml. A 17-fold excess (87 µl=429 nmol) is added to 5 mg (~1 ml=25 nmol) of the nanoparticles and the mixture incubated rotating at room temperature for 4.5 h. The unbound FITC is separated using a sephadex G-25 M PD 10 column (Amersham Bioscience) and 10 mM Na-carbonate buffer pH 8.5 as elution buffer. The eluted fraction of 3.5 ml contains fluorescein coupled nanoparticles.

Example 4

Measurement of FRET with Fluorescein-Coupled Nanoparticles

The fluorescein-coupled core (CePO$_4$)-shell (TbPO$_4$)-particles of example 3 and homogeneous LaPO$_4$:Ce,Tb of comparative example 1 were subjected to various spectroscopic analysis to determine the FRET efficiency.

The measurements were conducted with a FL3-22 spectrometer manufactured by Jobin Yvon with aqueous dispersions of the sample in optical cells having a width and depth of 1 cm each. The concentration was selected such that the optical density did not exceed 0.3.

Figure 3:
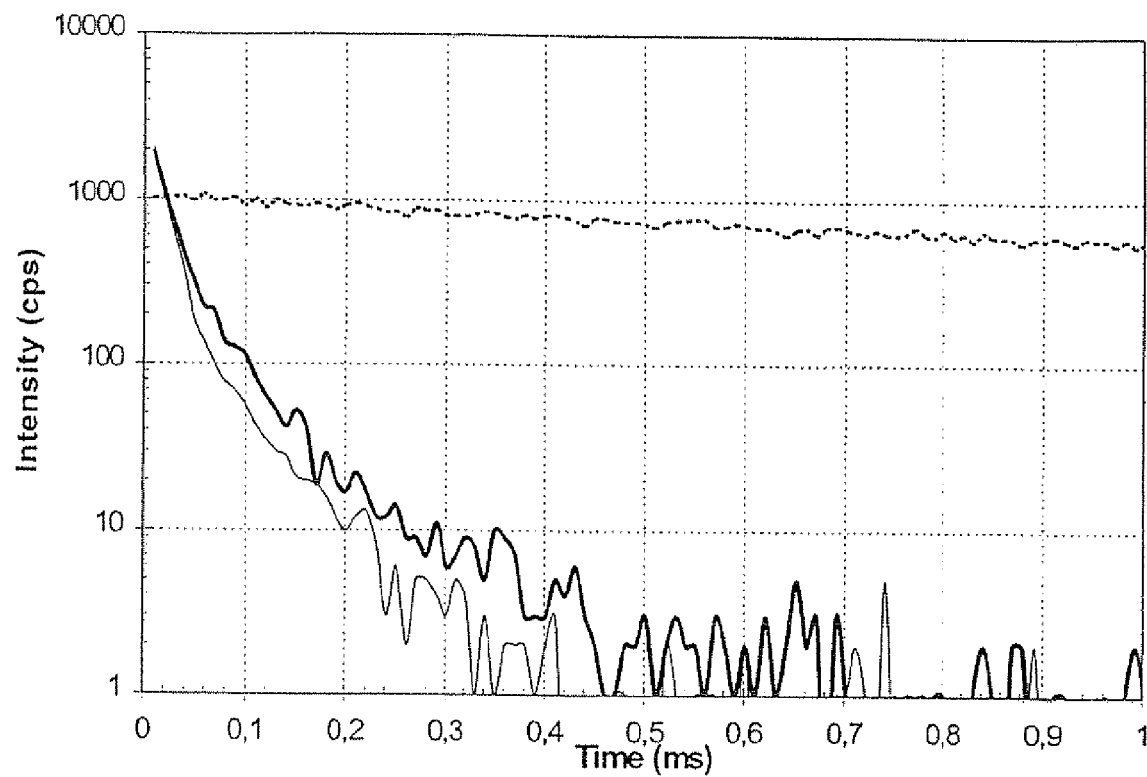
FIG. 3 shows two fluorescence decay curves of $CePO_4/TbPO_4$ core/shell particles according to the invention, which were modified and chemically coupled to fluorescein, respectively. As reference, the fluorescence decay curve of $CePO_4/TbPO_4$ core/shell particles which were not coupled to fluorescein is also shown.

FIG. 3 shows the decay curves of two particle types which were measured in TRF mode after pulsed excitation at 280 nm:

The dotted line represents the decay curve at 542 nm (Tb emission) of unmodified core (CePO$_4$)-shell (TbPO$_4$)-particles as obtained in example 1; half value 1.4 ms.

The bold line represents the decay curve at 542 nm of fluorescein-coupled core (CePO$_4$)-shell (TbPO$_4$)-particles as obtained in example 3; half value of 0.02 to 0.1 ms.

the thin line represent the decay curve at 520 nm (fluorescein emission) of fluorescein-coupled core (CePO$_4$)-shell (TbPO$_4$)-particles as obtained in example 3; half value of 0.02 to 0.06 ms.

Figure 4:
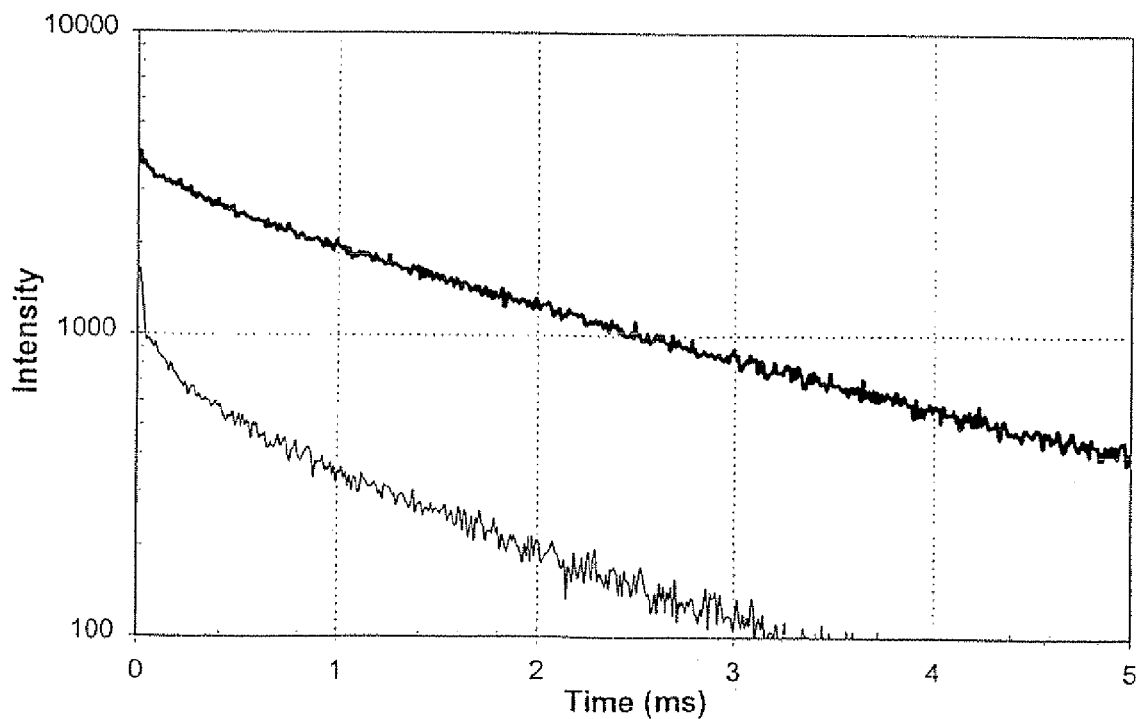
FIG. 4 shows the fluorescence decay curves of fluorescein-coupled, homogeneous $LaPO_4$:Ce, Tb particles (comparative example 1).

FIG. 4 shows the decay curves of fluorescein-coupled, homogeneous LaPO$_4$:Ce,Tb particles of comparative example 1 which were measured in TRF mode after pulsed excitation at 280 nm:

The bold line represents the decay curve at 542 nm (half value about 1.7 ms).

The thin line represents the decay curve of the same particles at 520 nm (half value about 1.0 to 1.5 ms).

The fluorescein-coupled core (CePO$_4$)-shell (TbPO$_4$)-particles of example 3 show much shorter fluorescence half values (at 542 nm 0.02 to 0.1 ms) than the particles of comparative example 1 (about 1.7 ms). This indicates that the core/shell structure of the particles according to the invention allows a much more efficient energy transfer to the acceptor molecule (fluorescein) thereby increasing the FRET efficiency. The fluorescence half value (about 1.4 ms) of unmodified core (CePO$_4$)-shell (TbPO$_4$)-particles thus is at least 14 times higher than observed for fluorescein-coupled core/shell particles of example 3.

The fluorescence half value of unmodified homogeneous LaPO$_4$:Ce,Tb nanoparticles (not coupled to fluorescein) is about 2.4 ms, i.e. about 1.5 times higher than observed for the corresponding fluorescein-coupled particles of comparative example 1 (at 542 nm about 1.7 ms). If this ratio (about 1.5/1) is compared with the ratio (about 14/1) shown by FIG. 3, the improvement in FRET efficiency obtained with the present invention becomes clear.

Figure 5A:
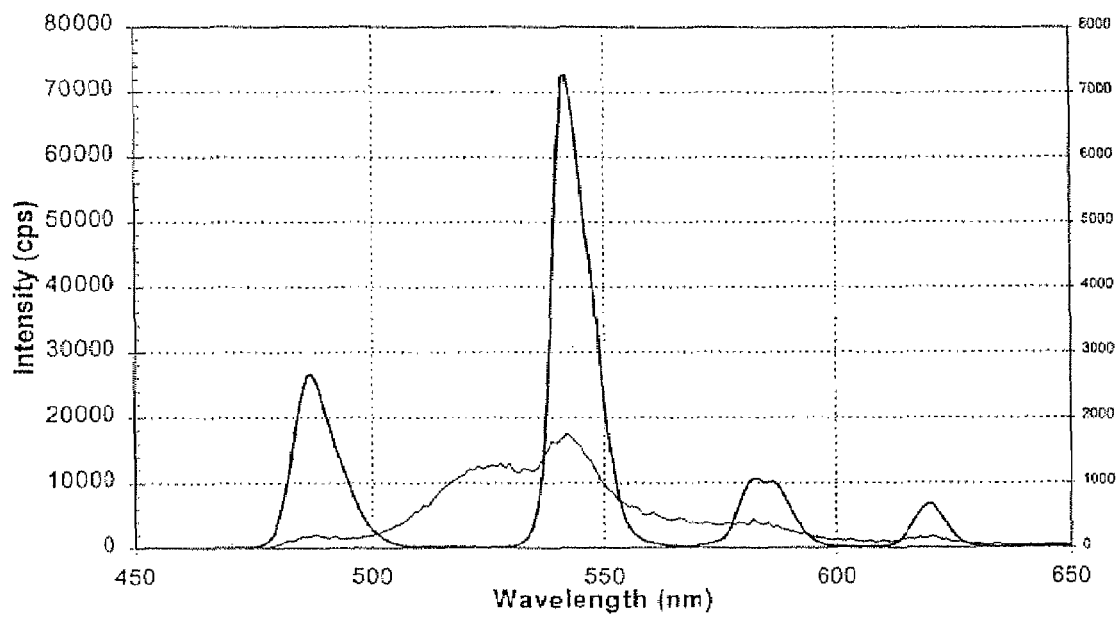
FIG. 5a shows two fluorescence spectra measured in time gated (TGF) mode of $CePO_4/TbPO_4$ core/shell particles according to the invention, which were not further modified or coupled to fluorescein, respectively.

FIG. 5a shows fluorescence spectra measured in TGF mode after pulsed excitation at 280 nm and a measurement delay of 40 μs after the last excitation pulse:

the bold line represents the spectrum of unmodified core (CePO$_4$)-shell (TbPO$_4$)-particles as obtained in example 1, and the thin line represents the spectrum of fluorescein-coupled core (CePO$_4$)-shell (TbPO$_4$)-particles as obtained in example 3.

The left intensity scale corresponds to the bold line and the right one to the thin line. The emission spectrum of the modified core/shell particles (example 3) is characterized by a very low intensity of the characteristic Tb$^{3+}$ band at 545 nm (reduced to about ¹/₄₀) and the appearance of a new broad band around 520 nm, which stems from fluorescein emission. After energy transfer of the excitation energy (280 nm) from Ce$^{3+}$ (core) to Tb$^{3+}$ (shell) luminescent centers, the latter thus initiate fluorescein luminescence by FRET.

Figure 5B:
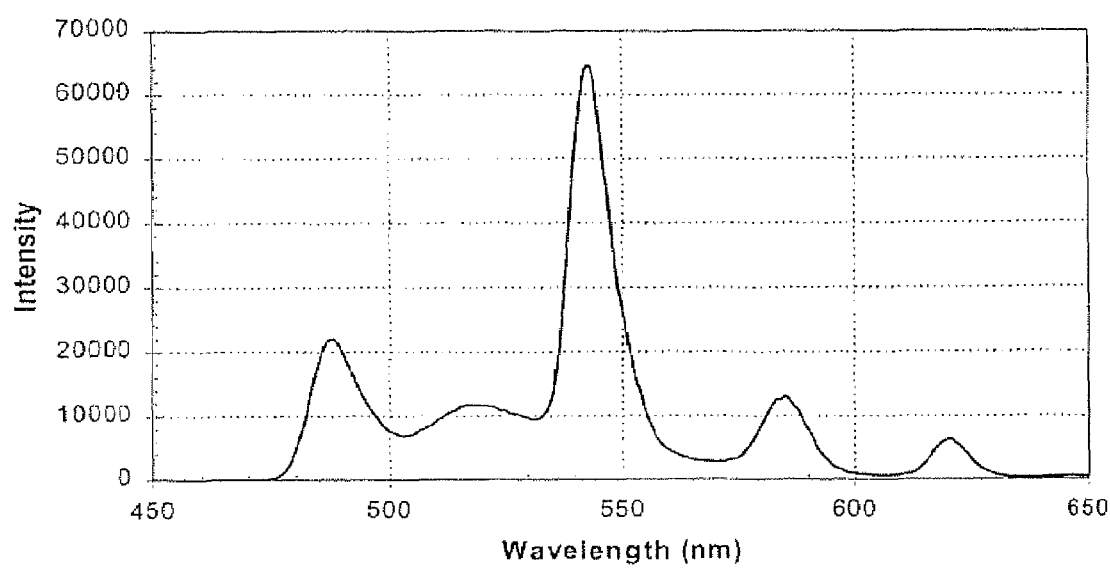
FIG. 5b shows one fluorescence spectrum measured in time gated mode of homogeneous $LaPO_4$:Ce, Tb nanoparticles (comparative example 1) at 520 nm and 542 nm, respectively.

FIG. 5b shows one fluorescence spectrum measured in TGF mode after pulsed excitation at 280 nm and a measurement delay of 40 μs after the last excitation pulse of the fluorescein-coupled, homogeneous LaPO$_4$:Ce,Tb of comparative example 1.

This spectrum also confirms the occurrence of FRET since a relatively broad emission band around 520 nm stemming from fluorescein can be observed. However, the donor emission as reflected by the characteristic Tb$^{3+}$ band at 545 nm is still much stronger than in FIG. 4a (thin line) which demonstrates the lower FRET efficiency.

Reference Example 2

Bioassays

The following reference examples demonstrate specific techniques for binding homogeneous nanoparticles to biomolecules and using the correspondingly labeled biomolecules in biological assays. Although the nanoparticles used are not according to the invention, these reference examples are fully transferable to core/shell particles as claimed. In this context a skilled person will be aware that surface modification techniques as shown below for homogeneous nanoparticles are preferably applied to core/shell particles which were synthesized in a similar manner, in particular with respect to the choice of solvent which typically binds to the surface of the nanoparticles obtained.

RE 2-1: Carboxy-Functionalisation of LaPO$_4$:Ce, Tb Nanoparticles

LaPO$_4$:Ce, Tb particles were prepared as described in comparative example CE1-1.

50 mg of these nanoparticles (about 140 nmol) are heated over 3 hours to 210° C. together with 5 ml ethylene glycol (about 180 mmol) and 5 μl sulfuric acid (96-98%) under stirring and inert gas. Alternatively, it is possible to use other diodes, preferably polyethylene glycols of various chain lengths, most preferably HO—(CH$_2$—CH$_2$—O)$_n$—OH, wherein n=2-9. The particles start to dissolute in ethylene glycol around 135° C. After completion of the treatment, a vacuum corresponding to about 1.5 mbar is applied followed by removing approximately half the ethylene glycol amount. This leads to a clear residue. Thereafter the residue is subjected to dialysis against water overnight (dialysis tubing Spectra/Por, 5-6.000 MWCO, Spectrum, the Netherlands).

0.5mL sulfuric acid (96-98%) is then added to a solution of 100 mg (about 300 nmol) of the obtained nanoparticles in 20 mL water. 1 mM KMnO$_4$ solution is added drop-wise to the resulting mixture until a decolouration of the violet colour can no longer be observed. Thereafter the same amount of KMnO$_4$ solution is newly added followed by stirring overnight (>12 h). Excess permanganate is reduced by the drop-wise addition of freshly prepared 1 mM sodium sulfite solution. The resulting mixture is subjected overnight to dialysis against 0.1 M MES, 0.5 M NaCl, pH 6.0 (dialysis tubing Spectra/Por, 5-6.000 MWCO, Spectrum, the Netherlands).

RE 2-2: Dealkylation with Bromotrimethylsilane 300 mg (about 850 nmol) of LaPO$_4$:Ce, Tb nanoparticles as prepared in comparative example CE1-1 were treated in the same manner as described in comparative example CE1-2.

RE 2-3: The Coupling of LaPO$_4$:Ce, Tb Nanoparticles with 11-bis(phosphorylmethyl)amino-undecanoic acid and 1,4-bis(3-aminopropoxy)butane 11-bis(phosphorylmethyl)amino-undecanoic acid is prepared by heating a mixture of 201 g 11-amino-undecanoic acid, 170 g phosphorous acid, 200 mL concentrated hydrochloric acid and 200 mL water to 100° C. followed by adding dropwise 324 g formaline (37%) over one hour and stirring for 1 hour at 100° C. After cooling to room temperature, the precipitated product is isolated by vacuum-assisted filtration and dried under vacuum. Thereby 334 g 11-bis(phosphorylmethyl)amino-undecanoic acid is obtained. Similarly useful are the corresponding acids having from 2-18 carbon atoms.

0.5 g (1.85 mol) 11-bis(phosphorylmethyl)amino-undecanoic acid is dissolved in 2mL ethylene glycol followed by adding 0.894 g (4.375 mmol) 1,4-bis(3-aminopropoxy)butane. After the formation of a clear solution (exothermic reaction), 35 mg (100 nmol) of LaPO$_4$:Ce, Tb nanoparticles obtained in RE 2-2 are added at 50° C. followed by heating to 125° C. At approximately 120° C. the particles dissolve completely. After 4 hours a clear, slightly brownish solution is obtained which remains clear even after cooling to room temperature. The reaction mixture is subjected to dialysis against 2×2 L 10 mM sodium carbonate buffer pH 8.5 (dialysis tubing Spectra/Por, 5-6000 MWCO, Spectrum, the Netherlands). The dialysate obtained contains the precipitated nanoparticles.

RE 2-4: Biotinylation of LaPO$_4$:Ce, Tb Nanoparticles of RE 2-3

6.2 mL (=5 mg or ~15 nmol) of the nanoparticle mixture obtained in RE 2-3 is reduced in volume by means of a rotary evaporator and concentrated to 4.81 mg/mL. While still rotating, the dispersion obtained is incubated over 4 hours with a 20-fold molar excess of biotin-X-NHS (sulfo-biotin-aminocaproic acid-N-hydroxy-succinimide ester, Calbiochem, Schwalbach, Germany) followed by dialysis against PBS buffer (8 mM K$_2$HPO$_4$; 150 mM NaCl; 2 mM Na$_2$HPO$_4$; pH 7.4) (dialysis tubing Spectra/Por, 5-6000 MWCO, Spectrum, the Netherlands). The dialysate obtained is slightly cloudy.

RE 2-5: Coupling of DNA Oligonucleotide to the LaPO$_4$:Ce, Tb Nanoparticles of RE 2-3

The nanoparticles obtained in RE 2-3 are activated with a 40-fold excess of sulfo-SIAB (Sulfosuccinimidyl(4-iodacetyl)aminobenzoate, Perbio Science Deutschland GmbH, Bonn, Deutschland): 7.5 mg (~25 nmol) amino-functionalised nanoparticles are newly buffered by means of a Centricon filtering unit (MW-exclusion at 50000, Millipore, Eschborn, Germany) in TSMZ-buffer pH 7.3 (0.1 M NaCl; 0.1 M triethanolamine-HCl; 0.02 M NaOH; 0.27 mM ZnCl$_2$; 0.1% Tween 20; 1 mM MgCl$_2$) and adjusted to a concentration of about 7 mg/mL. 50 µl of 20 mM sulfo-SIAB solution in water are added to the particle dispersion followed by 15 minutes of incubation at 25° C. The reaction is terminated by the addition of 12 µl 1 M glycine (12-fold excess) and the free sulfo-SIAB separated over a Sephadex G25 PD 10 column (Amersham Pharmacia Biotech, Freiburg, Germany). A DNA oligonucleotide having the sequence 5'-CCACGCTTGTGGGTCAAC-CCCCGTGG-3' and a thiol-modification at the 5'-terminus and a dabcyl-modification (4-(4-dimethylaminophenylazo)benzoyl) at the 3'-terminus, as well as a control DNA oligonucleotide differing only in the lacking dabcyl molecule at the 3'-terminus from the probe were ordered from Interactiva (Ulm, Germany). Equimolar amounts of DNA oligonucleotide and SIAB-activated nanoparticles were mixed and incubated over 3 hours at 25° C. and overnight at 4° C. The nanoparticles coupled to the DNA oligonucleotide were separated from non-coupled particles and free DNA oligonucleotide by means of FPLC (Fast Performance Liquid Chromatography). The coupled particles were stored in, 50 mM Tris-HCl, pH 7.4; 0.1% BSA at 4° C. As long as no target DNA is present, the molecule obtained folds in a hair-pin structure whereby both termini of the molecule are in close vicinity to each other and FRET can occur. Under these circumstances the nanoparticle fluorescence is quenched by dabcyl.

RE 2-6: Coupling of Anti-β-hCG Monoclonal Antibody to the LaPO$_4$:Ce, Tb Nanoparticles of RE 2-3

In the first place, the LaPO$_4$:Ce, Tb nanoparticles obtained in RE 2-3 are activated with a 30-fold molar excess of 2-Iminothiolan (2-IT, Traut's reagent, Perbio Science Deutschland GmbH, Bonn): 2 mL (~25 nmol, 4 mg/mL) of these particles were transferred in TSE-buffer pH 8.5 (0.04 M NaCl; 0.05 M triethanolamine-HCl; 0.04 M NaOH; 0.5 mM EDTA; 0.1% Tween 20; pH 8.5). For this purpose they are centrifuged three times 15 min at 3000 g, the supernatant is decanted and each remaining residue taken up in 700 µl TSE-buffer pH 8.5. These particles are incubated with 75 µl 10 mM 2-IT (in TSE-buffer pH 8.5) at 25° C. over 1 hour followed by terminating the reaction with 9 µl (12-fold excess) 1 M glycine. In order to separate the 2-IT excess, the resulting mixture is newly centrifuged three times over 15 min at 3000 g, followed by decanting the supernatant and resuspending the precipitate twice in 1 mL TSE-buffer pH 7.3 (0.1 M NaCl; 0.1 M Triethanolamin-HCL; 0.02 M NaOH; 1 mM EDTA; 0.1% Tween 20; pH 7.3) and after the third centrifugation in 250 µl TSE-buffer pH 7.3. At the same time an equimolar amount of monoclonal mouse antibody being specific for β-hCG (clone F199C1, Perkin-Elmer Life Sciences-Wallac Oy, Finnland) is activated with a 40-fold excess of SMCC (N-Succinimidyl-4-(N-Maleimido-methyl)-cyclohexane-1-carboxyxlate-Perbio Science Deutschland GmbH, Bonn): 750 µl anti β-hCG antibody (=25 nmol at a concentration of 5 mg/mL) are rebuffered by means of a Centricon filtering unit (MW exclusion at 50 000) in TSMZ-buffer pH 7.3 (0.1 M NaCl; 0.1 M triethanolamine-HCl; 0.02 M NaOH; 0.27 mM ZnCl$_2$; 0.1% Tween 20; 1 mM MgCl$_2$) and adjusted to a concentration of 7 mg/mL. 50 µl of 20 mM SMCC-solution in DMF (=1 mmol) are added to this antibody solution followed by incubation at 25° C. over 30 min. The reaction is terminated by the addition of 12 µL 1M glycine (12-fold excess) and the free SMCC is separated over a Sephadex G25 PD 10 ready-to-use column (Amersham Pharmacia Biotech, Freiburg, Germany). Finally, equimolar amounts of 2-IT-activated nanoparticle dispersion and SMCC-activated antibody solution are mixed and incubated for 3 hours at 25° C. and then overnight at 4° C. The antibody-coupled nanoparticles are purified from non-coupled particles and free antibodies by gel permeation chromatography on Superdex 200 (Amersham Pharmacia Biotech, Freiburg, Germany). 0.1M MES, 0.5M NaCl, pH 6.0 is used as buffering eluent. The retention time for the coupled nanoparticles is about 2 hours.

RE 2-7: Coupling of LaPO$_4$:Eu$^{3+}$ nanoparticles with hIL-2

LaPO$_4$:Eu$^{3+}$ nanoparticles were produced in TEHP as described in the literature (J. Phys. Chem. B 2000, 104, 2824-2828) with the sole difference that 1.76 g LaCl$_3$×7H$_2$O was used instead of the nitrate mentioned in this reference. 300 mg (~1 µmol) of these nanoparticles were heated under reflux together with 2.23 g (15 mmol) bromotrimethylsilane in 125 mL chloroform over 4 hours. The major part of bromotrimethylsilane excess and intermediate products formed is distilled off followed by hydrolysing the residue under slightly ammoniacal conditions. For this purpose the residue is treated with 6 mL water to which 100 µl ammonia (25%) was added, and stirred overnight. The resulting particles form a milky dispersion and sediment partially after several hours. 5 mg (=25 mmol, 106 µl) of these bromotrimethylsilane-treated nanoparticles were incubated over 1 hour at 37° C. under shaking with recombinant human IL-2 protein (R&D Systems, Minneapolis, Minn., USA) in 10 mM sodium carbonate-buffer pH 8.5 in a molar ratio of 2:1. Subsequently excess protein is separated by centrifuging the resulting mixture 6 times over 10 min at 3000 g, followed each by resuspending in 1 mL 10 mM sodium carbonate buffer pH 8.5. The LaPO$_4$:Eu$^{3+}$/IL-2 conjugate is stored at 4° C.

RE 2-8: Homogeneous Energy Transfer Assay for Detecting β-hCG with the Antibody-Coupled Nanoparticles of RE 2-6 as Donor and Fluorescence-Coupled Antibodies as Acceptor Coupling of anti-β-hCG antibodies to fluorescein:
Fluororeporter® FITC protein labelling kit produced by Molecular Probes was used for coupling fluorescein to anti-β-hCG antibodies (M15294, Perkin-Elmer Life Sciences, Wallac Oy, Finnland) according to the manufacturer's instructions. 0.5 mg antibodies were re-buffered by means of a Centricon filtering unit (MW exclusion at 50 000) in 0.2 M hydrogencarbonate buffer pH 9.0. The antibody solution is then incubated with a 25-fold excess of 5 mM fluorescein-isothiocyanate (FITC) solution (dissolved in a mixture of the same volume of DMF and 0.2 M hydrogencarbonate buffer pH 9.0) and incubated for 3 hours at room temperature. The FITC excess is separated over a ready-to-use Sephadex G25 PD 10 column (Amersham Pharmacia Biotech, Freiburg, Germany) and the antibody concentration and the ratio fluorescein/antibody are spectroscopically determined. 0.01% sodium azide and 0.1% BSA are added to the conjugate which is stored at 4° C.

Conducting the Assay:

50 µl β-hCG standards from a commercially available kit for the measurement of free β-hCG in serum (A007-101, Perkin-Elmer Life Sciences, Wallac Oy, Finnland) are incubated over 60 min at 25° C. together with 100 nmol of nanoparticle-antibody conjugates obtained in RE 2-6 and 100 nmol of fluorescein-coupled anti-β-hCG antibodies in 200 µL tris-HCl buffer, pH 7.4 in a UV-permeable 96-well microtiter plate (UVStar, Greiner). The two anti-β-hCG antibodies are directed against different epitopes of the β-hCG subunit. Thereafter the samples are measured in a fluorescence spectrometer (produced by Jobin Yvon, Fluorolog 3) under the following conditions: pulsed excitation at a wave length of 280 nm, emission: 542 nm, slit width: 5 nm, integration time 0.1 ms. The results obtained for the individual β-hCG concentrations are entered in a calibration curve. The β-hCG content of body samples can be measured in an analogous manner in serum samples by determining the concentration on the basis of this calibration curve.

RE 2-9 Homogeneous Competitive Energy Transfer Assay for Determining hIL-2 with the hIL-2-Coupled Nanoparticles (LaPO$_4$:Eu$^{3+}$) of RE 2-7 and Alexa Fluor 680-Coupled anti-hIL-2Rα-Chain Antibodies Coupling of Monoclonal anti-hIL-2Rα Chain Antibodies with Alexa Fluor 680:

1 mg monoclonal antibody 7G7B6 which specifically recognizes the α-chain of human interleukin-2 receptor (hIL-2α-chain) (ATCC, Rockville, USA) was dialysed against PBS, adjusted to a concentration of 2 mg/mL and labeled with Alexa Fluor 680 protein labelling kit (Molecular Probes Europe BV, the Netherlands) according to the instructions of the manufacturer. Using 0.1 M sodium bicarbonate buffer pH 8.3 as reaction buffer, the incubation was performed at room temperature over 1 hour. The coupled antibody is purified over a column contained in the kit using PBS-buffer with 0.2 mM Na-azide as eluent buffer. In a 1 cm optical cell the absorption (A) at 280 and 679 nm is measured in order to determine the protein concentration of the coupled antibody which is then calculated by means of the following formula:

$$M = \frac{(A_{280} - (A_{679} \times 0.05)) \times \text{dilution factor}}{2030000}$$

where 203 000 cm$^{-1}$M$^{-1}$ represents the molar extinction coefficient of IgG and 0.05 is the correction factor for the absorption of the dye at 280 nm is. The concentration of coupled antibody is 1.27 and is adjusted to 1 mg/mL (~6.5 µM) with PBS, 0.2 mM Na-azid. The coupled antibody is stored at 4° C. The labeling efficiency is calculated as follows.

$$\text{Mol dye per mol antibody} = \frac{A_{679} \times \text{dilution factor}}{184000 \times \text{protein concentration } M}$$

wherein 184 000 cm$^{-1}$M$^{-1}$ represents the molar extinction coefficient of Alexa Fluor 680 dye at 679 nm. The ratio of antibody/dye conjugate is 3.2.

Conducting the Assay:

The necessary dilutions of various components are obtained with 50 mM TSA-buffer (50 mM Tris-HCl pH 7.75; 0.9% NaCl; 0.05% NaN$_3$). 40 wells of UV-permeable microtiter plates (UVStar, Greiner) are in the first place incubated with BSA-solution (0.5%) over 1 hour at room temperature in order to saturate unspecific binding followed by adding a mixture of the LaPO$_4$:Eu$^{3+}$/IL-2 conjugate of example RE 2-7, Alexa Fluor 680-labelled anti-hIL-2α-chain antibody and recombinant hIL-2sRα protein (human IL-2 soluble receptor alpha, R&D Systems, Minneapolis, Minn., USA), each with a final concentration of 40 nM. 20 of these wells are charged with non-labelled hIL-2 protein in different concentrations the remaining 20 with a protein of no relevance for this assay. Each concentration is increased by 50 nM in order to test a concentration serial of 0-950 nM. The end volume of the reaction is in each case 200 µL. The incubation is performed in the darkness over 45 min at room temperature on a shaker. The signals are read with a Wallac 1420 Victor™ Multilabel Counter (Perkin-Elmer Life Sciences, Wallac Oy, Finnland) under the following conditions: Excitation: 340 nm, emission: 665 nm, time delay: 50 µs, time window: 200 µs and cycling time: 1000 µs. Each value is determined twice and corrected based on the results for unspecific binding obtained with the irrelevant protein. The measured values are plotted against the protein concentrations in a diagram resulting in a calibration curve, by means of which concentrations of human interleukine-2 can be determined. This is possible in an analogous manner for human body samples.

RE 2-10 Quantitative PCR Determination of Bacterial DNA by Intramolecular Energy Transfer with the DNA oligo Nucleotide-Coupled LaPO$_4$:Ce, Tb nanoparticles of RE 2-5

The primer and the probe for the quantitative DNA determination were specifically selected for RNA polymerase gene of Mycobacterium tuberculosis and produced by Interactiva (Ulm, Germany). The primer had the following sequences: forward 5'-GGCCGGTGGTCGCCGCG-3' backward 5'-ACGTGACAGACCGCCGGGC-3'.

Assay for Quantitative Determination of Bacterial DNA

For 50 µL PCR reactions, 50 nM of the nanoparticles (dabcyl-oligonucleotide-coupled) of RE 2-5 as probe, 500 nM each of both primers, 2 U Amplitaq Gold DNA Polymerase (Perkin-Elmer), 250 µM dATP, 250 µM dCTP, 250 µM dGTP, 500 µM dUTP, 4 mM MgCl$_2$, 50 mM KCl and 10 mM Tris-HCl pH 8.0 were mixed. Genomic M. tuberculosis DNA is amplified as DNA template with the same primers and cloned in a plasmid with the aid of Invitrogen Zero Blunt TOPO PCR Cloning Kit (Invitrogen BV/NOVEX, the Netherlands). To obtain a standard curve, 5 different concentrations of DNA plasmid of 1 pg to 100 ng are used as well as a reaction without DNA template. 30 reactions were prepared for each concentration so that, beginning after the 15$^{th}$ cycle, a sample could be drawn after each additional cycle for spectrometrically measuring the same. The reaction volume was 50 µL and the amplification was performed with a Thermocycler (PCR-System 2400, Perkin-Elmer) under the following reaction conditions: 10 min. at 95° C.; 15 to 45 cycles of 30 s at 95° C., 45 s at 56° C. and 30 s at 72° C. The samples were measured in a fluorescence spectrometer (produced by Jobin Yvon, Fluorolog 3) under the following conditions: pulsed excitation at a wave length of 280 nm, emission: 542 nm, slid width: 4 nm, time delay: 50 µs, repetition rate about 25 Hz. In the same manner it is possible to determine the half value of the terbium emission line. For this purpose the following conditions were used: excitation: 280 nm, emission: 542 nm, slit width: 5 nm, integration time: 0.1 ms. During the hybridism of probe and target DNA no intramolecular FRET occurs between the coupled nanoparticle and dabcyl. With increasing target DNA concentration, the Tb-fluorescence of the nanoparticle increases therefore with respect to the control sample without template. Simultaneously, the half value of the nanoparticle fluorescence life time is prolonged over the control sample without template DNA. These differences of both parameters can be plotted against the number of cycles to obtain a calibration curve for each DNA template concentration.

The invention claimed is:

1. Luminescent inorganic nanoparticles comprising:
   (a) a core comprising a first metal salt or oxide; and
   (b) a shell surrounding the core, wherein the shell is comprised of a second metal salt that is luminescent and has non-semiconductor properties, and
   wherein
   (i) said first metal salt or oxide is non-luminescent, or
   (ii) said first metal salt or oxide is capable of being excited by excitation energy and transferring said excitation energy to said second metal salt which emits the excitation energy as luminescence.

2. Luminescent nanoparticles according to claim 1, wherein the first metal salt of the core and the second metal salt of the shell comprise the same anion.

3. Luminescent nanoparticles according to claim 2, wherein the anion is selected from phosphates, sulfates, or fluorides.

4. Luminescent nanoparticles according to claim 1, having an average diameter based on their longest axis of less than 30 nm.

5. Luminescent nanoparticles according to claim 1, wherein the average thickness of the shell does not exceed the average diameter of the core.

6. Luminescent nanoparticles according to claim 1, wherein (a) the core is non-luminescent and (b) the shell comprises a luminescent metal atom.

7. Luminescent nanoparticles according to claim 6, wherein the shell comprises said luminescent metal atom as a predominant metal component.

8. Luminescent nanoparticles according to claim 7, wherein the core consists of $LaPO_4$ and the shell of $TbPO_4$.

9. Luminescent nanoparticles according to claim 7, wherein the shell comprises said luminescent metal atoms as a sole metal component.

10. Luminescent nanoparticles according to claim 6, wherein the shell comprises said luminescent metal atom as dopant of a non-luminescent host material.

11. Luminescent nanoparticles according to claim 6, wherein the luminescent metal atom is selected from Ce, Pr, Nd, Sm, Eu, Gd, Tb, Dy, Ho, Er, Tm, Yb, Cr, Mn, or a combination thereof.

12. Luminescent nanoparticles according to claim 1, wherein the core metal and the shell metal are selected from Ce, Pr, Nd, Sm, Eu, Gd, Th, Dy, Ho, Er, Tm, or Yb.

13. Luminescent nanoparticles according to claim 1, wherein the core metal is selected from Ce and the shell metal from Nd, Dy or Tb.

14. Luminescent nanoparticles according to claim 1, wherein the core metal is Yb and the shell metal Er.

15. Luminescent nanoparticles according to claim 1, wherein the core comprises the metal of the first metal salt or oxide as predominant metal component, or the shell comprises the metal of the second luminescent metal salt as predominant metal component, or both.

16. Luminescent nanoparticles according to claim 15, wherein the core comprises the metal of the first metal salt or oxide as a sole metal component, or the shell comprises the metal of the second luminescent metal salt as a sole metal component, or both.

17. Luminescent nanoparticles according to claim 1, wherein the core comprises the metal of the first metal salt or oxide as dopant of a host material, or the shell comprises the metal of the second luminescent metal salt as dopant of a host material, or both.

18. Luminescent nanoparticles according to claim 1, wherein the core consists of $LaPO_4$:Ce or $CePO_4$ and the shell of $TbPO_4$.

19. A dispersion comprising the nanoparticles according to claim 1 contained in a fluid or solid medium.

20. The dispersion of claim 19, wherein the fluid medium is selected from an organic or aqueous dispersion medium, coating composition, ink, dye, polymer composition, or aerosol.

21. The dispersion of claim 19, wherein the solid medium is selected from a coating, ink, dye, or polymer composition.

22. A (F)RET bioassay method comprising observing an absence, presence, or a change in intensity, of a fluorescence resonance energy transfer between a fluorescent donor and a fluorescent acceptor, wherein at least one of said fluorescent donor and fluorescent acceptor is a nanoparticle according to claim 1.

23. The (F)RET bioassay method of claim 22, wherein the method is used for detecting a nucleic acid.

24. A process for the preparation of luminescent inorganic nanoparticles comprising the steps of:
   preparing a first mixture comprising nanoparticle cores of a first metal salt or oxide in an organic medium,
   reacting said first mixture, an anion source for the shell to be formed and a second mixture comprising shell-forming metal ions and an organic complexing agent for said metal ions at a temperature of 50 to 350° C. until a shell has formed around said nanoparticles cores of a second metal salt;
the resulting luminescent inorganic nanoparticles comprising:
   (a) a core comprising a first metal salt or oxide; and
   (b) a shell surrounding the core, wherein the shell is comprised of a second metal salt that is luminescent and has non-semiconductor properties, and wherein
   (i) said first metal salt or oxide is non-luminescent, or
   (ii) said first metal salt or oxide is capable of being excited by excitation energy and transferring said excitation energy to said second metal salt which emits the excitation energy as luminescence.

25. The process according to claim 24, wherein the organic medium present in the first mixture and the organic complexing agent present in the second mixture are identical.

26. The process according to claim 24, wherein the organic medium and the complexing agent are selected from mono- or di-alkyl amines wherein the alkyl groups have from 4 to 20 carbon atoms, phosphororganic compounds, polyols or sulfoxides.

27. The process according to claim 24, further comprising the steps of synthesizing the nanoparticle cores in said organic medium followed by reacting the nanoparticle cores without prior isolation.

28. The process according to claim 24, wherein the anion source is included in excess molar amounts based on the stoichiometrically required amount for reacting with available shell-forming metal ions.

29. The process according to claim 28, wherein the anion source is selected from phosphate, sulfate, or fluoride.

* * * * *